(12) United States Patent
Lennox

(10) Patent No.: US 7,056,334 B2
(45) Date of Patent: Jun. 6, 2006

(54) METHODS AND APPARATUS FOR THERMALLY ACTIVATING A CONSOLE OF A THERMAL DELIVERY SYSTEM

(75) Inventor: Charles D. Lennox, Hudson, NH (US)

(73) Assignee: MedCool, Inc., Westwood, MA (US)

( * ) Notice: Subject to any disclaimer, the term of this patent is extended or adjusted under 35 U.S.C. 154(b) by 0 days.

(21) Appl. No.: 10/856,611

(22) Filed: May 28, 2004

(65) Prior Publication Data
US 2004/0243202 A1 Dec. 2, 2004

Related U.S. Application Data

(60) Provisional application No. 60/473,705, filed on May 28, 2003.

(51) Int. Cl.
*A61F 7/00* (2006.01)
(52) U.S. Cl. .................. 607/96; 607/104; 607/108; 607/114
(58) Field of Classification Search .............. 607/96, 607/104–107, 114, 109, 110, 111, 112, 113, 607/108
See application file for complete search history.

(56) References Cited

U.S. PATENT DOCUMENTS

| | | | |
|---|---|---|---|
| 3,587,577 A | 6/1971 | Smirnov et al. | 128/254 |
| 5,097,829 A | 3/1992 | Quisenberry | 607/105 |
| 5,174,285 A | 12/1992 | Fontenot | 607/104 |
| 5,862,675 A | 1/1999 | Scaringe et al. | 62/196.3 |
| 5,871,526 A | 2/1999 | Gibbs et al. | 607/104 |
| 6,086,609 A | 7/2000 | Buckley | 607/104 |
| 6,149,674 A | 11/2000 | Borders | 607/96 |
| 6,178,562 B1 | 1/2001 | Elkins | 2/458 |
| 6,508,831 B1 | 1/2003 | Kushnir | 607/104 |
| 6,517,510 B1 | 2/2003 | Stewart et al. | 604/31 |
| 6,620,187 B1 | 9/2003 | Carson et al. | 607/104 |
| 6,673,098 B1 * | 1/2004 | Machold et al. | 607/96 |
| 2003/0163183 A1 | 8/2003 | Carson | 607/108 |
| 2003/0229385 A1 | 12/2003 | Elkins | 607/104 |

OTHER PUBLICATIONS

Game Ready, Advanced Injury Treatment, www.gameready.com, Search done on Jan. 25, 2005, pp. 1-3.

* cited by examiner

*Primary Examiner*—Rosiland Rollins
(74) *Attorney, Agent, or Firm*—Thomas J. Engellenner; Charlton Shen; Nutter McClennen & Fish LLP

(57) ABSTRACT

A thermal delivery system includes a base unit having a thermal regulation source and a console configured to deliver cooling fluid to a body-cooling device to induce hypothermia and aid in resuscitation of a patient. When a user docks the console with the base station, the console thermally contacts the thermal regulation source. The thermal regulation source alters the temperature of fluid held by the console for an indefinite period of time. In the case where a patient, at a location remote from the thermal delivery system, requires induction of hypothermia, a user detaches the console from the base station and transports the console to the patient's location. The configuration of the thermal delivery system allows the base station to thermally adjust the temperature of the fluid held by the console for an extended period of time, thereby minimizing a delay in transporting a console having the thermally adjusted fluid to the patient.

25 Claims, 13 Drawing Sheets

METHODS AND APPARATUS FOR THERMALLY ACTIVATING A CONSOLE OF A THERMAL DELIVERY SYSTEM

RELATED APPLICATIONS

This application claims benefit of U.S. Provisional Application Ser. No. 60/473,705, filed May 28, 2003, the entire teachings of which are incorporated herein by reference.

BACKGROUND

Application of thermal therapy to a patient after an injury or trauma helps to minimize tissue damage of the patient following the injury. For example, application of cold therapy to a patient, such as an athlete, after incurrence of a muscle injury helps to reduce pain, muscle spasms, tissue damage, and swelling at the injury site. In another example, patients that suffer from stroke, cardiac arrest, or trauma, such as head trauma, as well as patients that have undergone invasive brain or vascular surgery, are at risk for ischemic injury. Ischemic injury occurs as a result of a lack of oxygen (e.g. lack of oxygenated blood) to an organ, such as caused by a blockage or constriction to a vessel carrying blood to the organ. Induction of systemic hypothermia (e.g., a hypothermic state) in a patient may minimize ischemic injury when the patient suffers from a stroke, cardiac arrest, heart attack, trauma, or surgery. In the case where the patient suffers a heart attack, the effectiveness of hypothermia is a function of the depth (e.g., within a temperature range between approximately 30° C. and 35° C. for example) and duration of the hypothermic state as applied to the heart. The effectiveness of the hypothermia is also a function of the amount of time that elapses between the original insult (e.g., heart attack) and achievement of protective levels of hypothermia. Also, for trauma and stroke patients, hypothermia aids in controlling swelling of the patient's brain.

In such cases, patients conventionally receive cold or hypothermic therapy by way of cooling devices. Typical cooling devices include heat exchange structures that receive cooling fluid from a console. For example, in the case of an athletic injury, a heat exchange pad contacts an athlete's skin in a location in proximity to a muscle injury. The console pumps cooling fluid to the heat exchange pad to reduce the temperature of the patient's tissue in the vicinity of the injury.

In one typical console used with a cooling device, such as the console used in the GAME READY Accelerated Recovery System (Game Ready Inc., Berkeley, Calif.) a user fills the console with an ice and water mixture to prepare the console for operation. During operation, a user places a cooling pad in contact with an injured area of a patient or athlete and couples the cooling pad with the console. The user then activates the console that in turn, circulates the ice-cooled water within the console through the cooling pad. The ice-cooled water reduces the temperature of the pad and reduces the temperature of the injury site of the patient to minimize tissue swelling and damage.

In another typical console used with a cooling device, such as used in inducing hypothermia in a patient, includes a reservoir containing refrigeration or cooling coils attached to a refrigerant. During operation, the console reduces the temperature of the refrigeration coils by circulating a refrigerant or low temperature fluid within the refrigeration coils. The refrigeration coils, in turn, reduce the temperature of a fluid contained by the reservoir. The console delivers the cooled fluid to a body-cooling device placed in contact with a patient. The cooled fluid reduces the temperature of the body-cooling device and, in turn, reduces the temperature of the injury site of the patient to minimize tissue swelling and damage.

SUMMARY

Conventional consoles for inducing an optimal therapeutic temperature in the body of a patient suffer from a variety of deficiencies.

For example, as indicated above, in certain, conventional consoles, a user fills the console with an ice and water mixture to prepare the console for operation. In such conventional consoles, the ice reduces the temperature of the water for provision to a cooling device. The conventional consoles do not include a temperature adjustment device that reduces the temperature of the water within the console. As such, prior to using the console, a user must know when he will need to use the console and have access to both water and ice to fill the console. In order to utilize the console in an emergency situation, such as to induce hypothermia in a patient at risk for ischemic injury, however, the console must contain a water and ice mixture at a moment's notice in order to minimize delay in transporting the console to the patient. Because conventional consoles require a user to retrieve both water and ice to fill the console and do not include a temperature adjustment device to maintain the water temperature in a cooled state for a prolonged amount of time, the conventional consoles increase the delay in transporting the console to the patient. Such a delay, in an emergency setting, can lead to irreversible tissue damage in the patient.

Also as indicated above, certain consoles used with a cooling device to induce hypothermia in a patient include a reservoir containing refrigeration or cooling coils attached to a refrigerant source. During operation, the console circulates a refrigerant from the refrigerant source within the refrigeration coils to reduce the temperature of a fluid held by a reservoir of the console. Such a configuration allows the console to maintain the temperature of the fluid in a cooled state for a prolonged period of time, thereby minimizing delay in transporting the console to a patient at risk for ischemic injury. However, because the aforementioned consoles include both cooling coils and a refrigerant source, the refrigerant source increase the weight of the console and reduces or limits portability of the console, particularly outside of a hospital or emergency care setting. For example, a user can have difficulty in transporting a relatively heavy console (e.g., a console including the refrigerant source) from a hospital to an ambulance for further transport to a patient in a pre-hospital setting.

By contrast, embodiments of the present invention significantly overcome such deficiencies and provide techniques for thermally activating a console of a thermal delivery system. The thermal delivery system includes a base unit having a thermal regulation source, such as a refrigeration unit, and a console configured to deliver cooling fluid to a body-cooling device to induce hypothermia and aid in resuscitation of a patient. When a user docks the console with the base station, the console thermally contacts the thermal regulation source. The thermal regulation source alters or reduces the temperature of fluid held by the console for an indefinite period of time. In the case where a patient, at a location remote from the thermal delivery system, requires induction of hypothermia to reduce a risk for ischemic injury, a user detaches the console from the base station and transports the console to the patient's location.

The configuration of the thermal delivery system allows the base station to thermally adjust the temperature of the fluid held by the console for an extended period of time, thereby minimizing a delay in transporting a console having the thermally adjusted fluid to the patient. Furthermore, the configuration of the thermal delivery system orients the thermal regulation source within the base station, separate from the console, thereby minimizing the weight of the console and providing ease of transport to a patient location.

In accordance with one embodiment of the invention, the console provides for rapid obtainment of an optimal body temperature in a patient undergoing resuscitation and does not significantly interfere with resuscitation of the patient according to generally accepted resuscitation practices.

In one arrangement, a thermal delivery system includes a base station having a base station thermal conductor and a thermal regulation source in thermal communication with the base station thermal conductor. The thermal delivery system also includes a console detachably coupled to the base station. The console has a reservoir configured to hold a fluid, a console thermal conductor coupled to the reservoir and in thermal communication with the base station thermal conductor of the base station, and a pump in fluid communication with the reservoir. The console thermal conductor is configured to exchange thermal energy with the base station thermal conductor. The pump is configured to deliver fluid from the reservoir to a body temperature regulation device. The configuration of the thermal delivery system allows the base station to thermally adjust the temperature of the fluid held by the console for an indefinite period of time, thereby minimizing a delay in transporting a console having the thermally adjusted fluid to the patient. Furthermore, the configuration of the thermal delivery system orients the thermal regulation source within the base station, separate from the console, thereby minimizing the weight of the console and providing ease of transport to a patient location.

One embodiment of the invention includes a thermal delivery system for rapidly obtaining an optimal body temperature in a patient in the emergency care setting. In one arrangement, the thermal delivery system maintains an optimal body temperature for an indefinite period of time thereafter. The thermal delivery system includes a console that is small enough and light enough to be hand carried to a stricken patient, and to then be hand carried and operated in close proximity to the patient during patient transport and while the patient is in the care of the emergency department of a hospital, and to operate by internal electrical and thermal batteries for a period of time sufficient to provide initial emergency care for the patient. The thermal delivery system includes a base station that operates the console substantially indefinitely independent of the state of the internal electrical and thermal batteries within the console, and a power source for charging or recharging the internal electrical and thermal batteries within the console.

In accordance with another aspect of embodiments of the invention, an apparatus includes a console that is small enough and light enough to be hand carried to a stricken patient, and to then be hand carried and operated in close proximity to the patient during patient transport and/or while the patient is in the care of the emergency department of a hospital, and to operate by internal electrical and thermal batteries for a period of time sufficient to provide initial emergency care for the patient. In one arrangement, the apparatus induces hypothermia in a patient's body such that the brain of the patient is cooled first and to a greater degree than the rest of the patient's body. In another arrangement, the apparatus effectively cools the head of a patient, thereby cooling the body of the patient.

In accordance with another embodiment of the invention, is an apparatus for resuscitation that allows substantially rapid induction of hypothermia in a patient's body to a predetermined temperature and then maintenance of the patient's body at the predetermined temperature for an extended period of time. The apparatus includes a head-cooling device, a body temperature sensor, a console, and a base station, whereby the console includes a single use cassette comprising an ice forming means, cooling fluid, a pump head, an aspiration port, a means for insertably removing and replacing the cassette into and out of the console, and an umbilical connection means. The console further includes a pump motor for actuating the pump head of the cassette, an aspiration pump, control circuitry, an electrical battery, and a means to connect the head-cooling device and the body temperature sensor to the console. The pump motor and pump head provides a means for supplying cooling fluid from the cassette to the head-cooling device under positive gage pressure, and whereby the aspiration pump provides a means for scavenging cooling fluid from the head-cooling device and returning the scavenged cooling fluid to the cassette by providing a negative gage pressure within the cassette. The control circuitry controls the operation of the pump motor and the aspiration pump according to signals received from the body temperature sensor in order to control body cooling. The base station and ice forming means in the cassette work in an operational relationship to make ice within the cassette thereby providing a thermal battery, in one arrangement.

In one arrangement the thermal delivery system is configured as an apparatus for resuscitation including a base station and a console. The console configured to transported (e.g., hand carried) to a stricken patient, placed and operated in close proximity to the patient during patient transport and when the patient arrive at and is in the care of the emergency department of a hospital. The console includes a defibrillator and a body-cooling device to rapidly lower the temperature of the body of the patient. The console also includes a means to be operated for more than one hour on internal electrical and thermal batteries, a means to dock with the base station, whereby the base station provides a means to operate the console for an extended period of time, independent of the state of the internal electrical and thermal batteries within the console, and further provides a means to charge or recharge the internal electrical and thermal batteries within the console.

In accordance with another aspect of this invention, is a life support apparatus including a mobile console. In one arrangement, the life support apparatus includes a body temperature management system, and one or more of the following: a defibrillating means, an EKG monitoring means or a heart monitoring means, a physiological monitoring means, a fluid infusion means, an inhalation therapy means, and an integrated user control and display panel.

In accordance with another aspect of this invention, is a method of resuscitation. A user transports, to a stricken patient, an apparatus that is configured to lower the patient's body temperature to a predetermined level, and then maintain the patient's body temperature at the predetermined level for an extended period of time. The apparatus includes a head-cooling device, a console, and a body temperature sensor. In the method the user initiates resuscitation, places the head-cooling device on the head of the patient, and connects the head-cooling device to the console. The user activates the console to initiate a cool down mode of operation of the apparatus. In one arrangement, when engaged in the cool down mode of operation, the apparatus provides a substantially continuous flow of cooling fluid from the console to the head-cooling device. The user then places the body temperature sensor on the patient's body and connects the body temperature sensor to the console either before activation of the system, or after activation of the system and before the patient's body temperature reaches the predetermined temperature. When the patient's body reaches the predetermined temperature, the console enters a temperature maintenance mode of operation. In one arrangement, the temperature maintenance mode of operation includes providing an intermittent flow of cooling fluid from the console to the head cooling device, whereby the intermittence of the flow of cooling fluid is adjusted by control algorithms within the control circuits of the console according to signals received from the body temperature sensor in order to maintain the patient's body temperature at the predetermined level.

In accordance with another aspect of this invention, is a method of resuscitation. A user transports, to a stricken patient, an apparatus that is configured to lower the patient's body temperature to a predetermined level, and then maintain the patient's body temperature at the predetermined level for an extended period of time. The apparatus includes a head-cooling device, a console, and a body temperature sensor. In the method the user initiates resuscitation, places the head-cooling device on the head of the patient, and connects the head-cooling device to the console. The user activates the console to initiate a cool down mode of operation of the apparatus. In one arrangement, when engaged in the cool down mode of operation, the apparatus provides a substantially continuous flow of cooling fluid from the console to the head-cooling device at a predetermined rate. The user then places the body temperature sensor either on or within the patient's body and connects the body temperature sensor to the console either before activation of the system, or after activation of the system and before the patient's body temperature reaches the predetermined temperature. When patient's body reaches the predetermined temperature, the console enters a temperature maintenance mode of operation, whereby the temperature maintenance mode of operation wherein the apparatus provides a substantially continuous flow of cooling fluid from the console to the head cooling device at a flow rate, whereby the flow rate is adjusted by control algorithms within the control circuits of the console according to signals received from the body temperature sensor in order to maintain the patient's body temperature at the predetermined level.

In accordance with another aspect of this invention, is a method of resuscitation. A user transports, to a stricken patient, an apparatus that is configured to lower the patient's body temperature to a predetermined level, and then maintain the patient's body temperature at the predetermined level for an extended period of time. The apparatus includes a head-cooling device, a console, and a body temperature sensor. In the method the user initiates resuscitation, places the head-cooling device on the head of the patient, and connects the head-cooling device to the console. The user activates the console to initiate a cool down mode of operation of the apparatus. In one arrangement, when engaged in the cool down mode of operation, the apparatus provides a substantially continuous flow of cooling fluid at a predetermined temperature above but near zero degrees centigrade from the console to the head-cooling device. The user then places the body temperature sensor on the patient's body and connects the body temperature sensor to the console either before activation of the system, or after activation of the system and before the patient's body temperature reaches the predetermined temperature. When the patient's body reaches the predetermined temperature, the console enters a temperature maintenance mode of operation. During the temperature maintenance mode of operation, the apparatus provides a substantially continuous flow of cooling fluid from the console to the head cooling device, whereby the temperature of the cooling fluid is adjusted by control algorithms within the control circuits of the console according to signals received from the body temperature sensor in order to maintain the patient's body temperature at the predetermined level.

In accordance with another aspect of this invention, is a method of resuscitation. A user transports, to a stricken patient, an apparatus that is configured to lower the patient's body temperature to a predetermined level, and then maintain the patient's body temperature at the predetermined level for an extended period of time. The apparatus includes a head-cooling device and a battery operated console. The user initiates resuscitation, places the head-cooling device on the head of the patient, connects the head-cooling device to the console, and activates the console. The user completes resuscitation of the patient and docks the small battery operated console with a base station. The base station includes a means of operating the battery operated console for an indefinite period of time independent of the state charge of the batteries within the battery operated console.

In accordance with another aspect of this invention, is a method of resuscitation. A user transports, to a stricken patient, an apparatus that is configured to lower the patient's body temperature to a predetermined level, and then maintain the patient's body temperature at the predetermined level for an extended period of time. The apparatus includes a head-cooling device and a battery operated console. The user initiates resuscitation, places the head-cooling device on the head of the patient, connects the head-cooling device to the console, and activates the console. The user completes resuscitation of the patient, deactivates the battery operated console, disconnects the head-cooling device from the small battery operated console, connects the head-cooling device to a second console that is not battery operated, and activates the second console to resuming cooling of the patient.

In accordance with another aspect of this invention, is a method of resuscitation. A user transports, to a stricken patient, an apparatus that includes a small battery operated console configured to a defibrillate the patient, lower the patient's body temperature to a predetermined level, and then maintain the patient's body temperature at the predetermined level for an extended period of time. The console includes a head-cooling device connectable to the battery operated console by an umbilical. The user initiates resuscitation by defibrillating the patient with the defibrillator provided by the battery operated console. The user places the head-cooling device on the head of the patient, connects the head-cooling device to the battery operated console, and activates the cooling means of the battery operated console. The user completes resuscitation of the patient and docks the small battery operated console with a base station whereby the base station includes a means for operating the battery operated console for an indefinite period of time independent of the state of batteries within the battery operated console.

In accordance with another aspect of this invention, is a method of resuscitation. A user transports, to a stricken patient, an apparatus that includes a small battery operated console configured to a defibrillate the patient, lower the patient's body temperature to a predetermined level, and then maintain the patient's body temperature at the predetermined level for an extended period of time. The console includes a head-cooling device connectable to the battery operated console by an umbilical. The user initiates resuscitation by defibrillating the patient with the defibrillator provided by the battery operated console. The user places the head-cooling device on the head of the patient, connects the head-cooling device to the battery operated console, and activates the cooling means of the battery operated console. The user completes resuscitation of the patient, deactivates the battery operated console, and disconnects the head-cooling device from the small battery operated console. The user then connects the head-cooling device to a second console that is not battery operated and activates the second console to resume cooling of the patient.

In another embodiment of the invention the thermal delivery system is configured a part of a resuscitation kit having a console, a base station, a head-cooling device, and directions for use.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments of the present invention provide techniques for thermally activating a console of a thermal delivery system. The thermal delivery system includes a base unit having a thermal regulation source, such as a refrigeration unit, and a console configured to deliver cooling fluid to a body-cooling device to induce hypothermia and aid in resuscitation of a patient. When a user docks the console with the base station, the console thermally contacts the thermal regulation source. The thermal regulation source alters or reduces the temperature of fluid held by the console for an indefinite period of time. In the case where a patient, at a location remote from the thermal delivery system, requires induction of hypothermia to reduce a risk for ischemic injury, a user detaches the console from the base station and transports the console to the patient's location. The configuration of the thermal delivery system allows the base station to thermally adjust the temperature of the fluid held by the console for an extended period of time, thereby minimizing a delay in transporting a console having the thermally adjusted fluid to the patient. Furthermore, the configuration of the thermal delivery system orients the thermal regulation source within the base station, separate from the console, thereby minimizing the weight of the console and providing ease of transport to a patient location.

Figure 1:
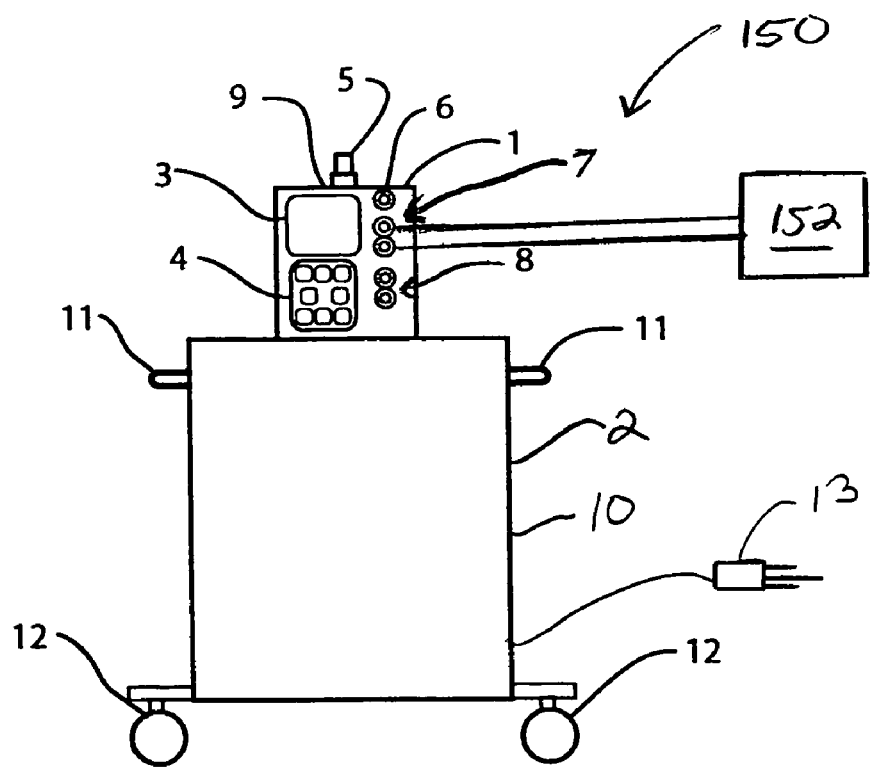
FIG. 1 depicts a front view of a thermal delivery system, according to one embodiment of the invention.
Figure 2:
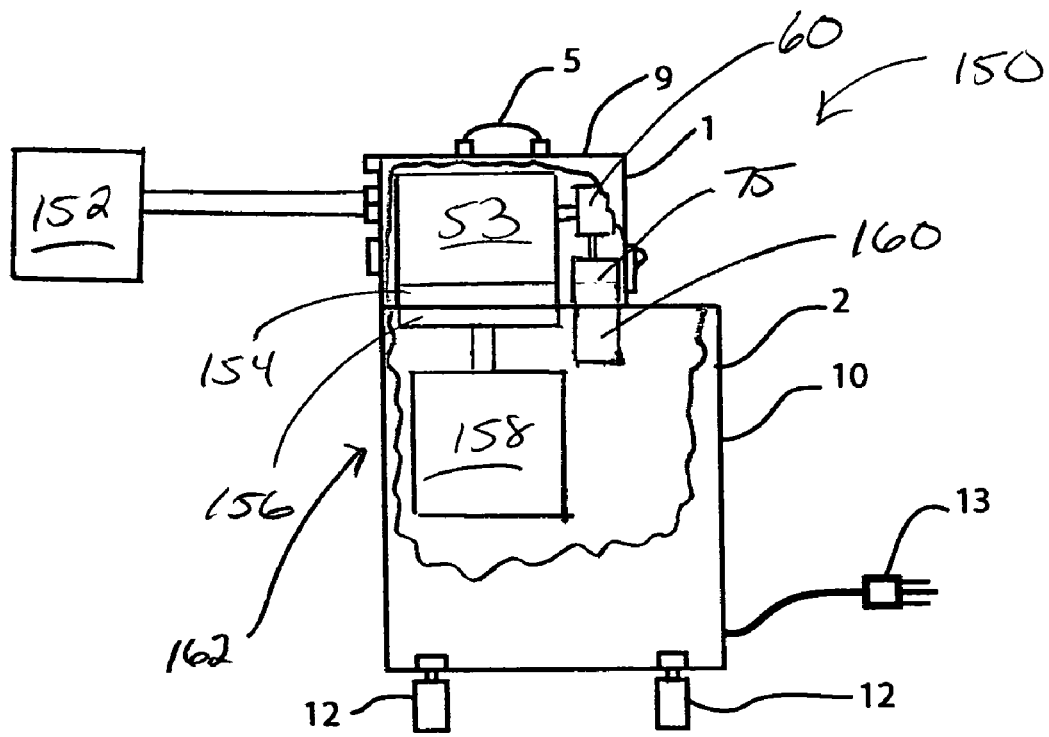
FIG. 2 illustrates a side, sectional view of the thermal delivery system of FIG. 1.

FIGS. 1 and 2 illustrate, according to one embodiment of the invention, a thermal delivery system 150 having a base station 2, a console 1, such as a small portable console 1, docked with the base station 2, and a body-cooling device 152. The console 1 contains a cooling fluid and is configured to deliver the cooling fluid to the body-cooling device 152, thereby allowing the body-cooling device to induce local or global hypothermia in a patient, for example, in a pre or post hospital setting. For example, in one arrangement, the body-cooling device is configured to induce protective levels of hypothermia in a patient's brain within approximately 5 to 30 minutes. In another example, the body-cooling device 152 is configured to induce protective levels of hypothermia in a patient's body within 30 to 90 minutes by lowering patient body temperature to a temperature between approximately 30 and 37° C. The base station 2 includes a thermal charging assembly configured to alter (e.g., reduce) the temperature of the fluid held by the console 1. The thermal delivery system 150 provides for relatively rapid manipulation of body temperature of a patient or subject.

In one arrangement, the console 1 includes a housing 9 having a display panel 3 and a control panel 4. The display panel 3 provides a user with graphical and alpha/numeric information on the status and operation of the console 1. The control panel 4 provides the user with an input, such as a keypad, to set operational parameters of the console 1 (e.g., body temperature of the patient, duration of therapy, etc.) and to control the operation of the console 1.

The console 1 also includes a carrying handle 5 that allows a user to separate or de-dock the console 1 from the base station and transport the console 1 to a patient location (e.g., a geographic location relatively remote from the base station 2). The handle 5 allows a user to hand carry the console 1 to a stricken patient and operate the console 1 in close proximity to the patient during patient transport. The console 1 further has a temperature sensor receptacle 6 for connecting a body temperature sensor to the system 150, a cooling device receptacle 7 for connecting a cooling device to the system (e.g., via an umbilical), and a secondary device receptacle 8 for attaching either a second cooling device or defibrillator electrode paddles to the system 150.

As shown in FIG. 2, the console 1 includes a cassette or reservoir 53 having a console thermal conductor 154, a pump 75, and a battery 75. The reservoir 53 is configured to hold a cooling fluid for thermal application to a patient via the body-cooling device 152. For example, the reservoir 53 stores the cooling fluid as a liquid, such as water, or as a gas. The console thermal conductor 154 is configured to exchange thermal energy with the base station 2 and transmit the thermal energy to the fluid within the reservoir 53. For example, in one arrangement, the console thermal conductor 154 in conjunction with the base station 2 reduces a temperature of the fluid within the reservoir to cool the fluid. The pump 60 is fluidly connected to the reservoir 53 and electrically coupled to the battery 75. In one arrangement, the pump 60 circulates cooled fluid from the reservoir 53 to a body-cooling device 152 to reduce the temperature of a patient in contact with the body-cooling device 152. The battery 75 provides, for example, power to the console 1 and the pump 60 and allows operation of the pump 60 when the console 1 disengages or decouples from the base station 2. In one arrangement, the battery 75 allows operation of the console 1 and the pump 60 for a time period of greater than one hour.

In one arrangement, the reservoir 53 and console thermal conductor 154 form a thermal battery. The base station 2 is configured to charge the thermal battery (e.g., modify the temperature of the thermal battery and the fluid within the thermal battery) when the console 1 docks with the base station 2. After the base station 2 charges the thermal battery, the console 1, in turn, can provide cooled fluid to a body-cooling device 152 for an extended period of time and at a location relatively remote from the base station 2 (e.g., in a the pre-hospital setting).

In one arrangement, the base station 2 includes a cabinet 10, handles 11, and casters 12 for moving the base station 2 from a storage location to a patient location. The base station 2 also includes a base station thermal conductor 156 and a thermal regulation source 158. In combination, the base station thermal conductor 156 and a thermal regulation source 158 form a thermal charging assembly. The base station thermal conductor 156 thermally contacts the console thermal conductor 154 when the console 1 docks with the base station 2. The base station thermal conductor 156 is configured to adjust the temperature of the console thermal conductor 154 to, in turn, modify the temperature of the fluid within the reservoir 53. The thermal regulation source 158 adjusts or modifies a temperature of the thermal battery (e.g., the base station thermal conductor 156) of the console 1. For example, in one arrangement, the thermal regulation source 158 is a solid-state refrigeration apparatus. In another arrangement, the thermal regulation source 158 is a gas based refrigeration apparatus.

The base station 2 also includes a power supply 160 that provides power to the base station 2 and to the console 1. The base station 2 includes an electrical cord 13 configured to insert into a wall outlet and carry current from the outlet to the power supply 160, for example. The power supply 160, in one arrangement, provides power to the thermal regulation source 158 to allow operation of the thermal regulation source 158. The power supply 160 also provides either charging or recharging to the electrical battery 75 of the console 1. For example, when the console 1 docks with the base station 2 the battery 75 contacts and receives current from the power supply 160. In one arrangement, when the console 1 docks with the base station 2, the power supply 160 operates all mechanical and electrical components within the console 1 independent from the state of charge of the electrical 75 within the console 1.

When the console 1 docks with the base station 2, the console thermal conductor 154 thermally couples to the thermal regulation source 158, via the base station thermal conductor 156, and the battery 75 of the console 1 electrically couples to the power source 160 of the base station 2. As a result of the docking, the thermal regulation source 158 adjusts the temperature of the console thermal conductor 154 to reduce the temperature of the fluid within reservoir 53 to a preset level (e.g., charge the thermal battery) and continuously maintain the temperature of the fluid at the preset level. Also as a result of the docking, the power source 160 provides a source of electrical power to the console 1, via the electrical cord 13 of the base station 2 (e.g., when inserted into a wall outlet) and the battery 75 of the console 1, to operate the electrical components (e.g., pump 60) within the console 1. A user can operate the console 1 when docked to the base station 2 for an extended period of time to provide for patient cooling via the body-cooling device 152.

Additionally, when the console 1 docks with the base station 2, the base station 2 charges the electrical battery 75 of the console 1. Such charge allows a user to de-dock the console 1 from the base station 2, transport the console to a patient at a remote location (e.g., remote relative to the base station 2), and operate the console 1 deliver cooling fluid (e.g. as cooled by the base station) to a body-cooling device 152 to provide body cooling to the patient. In one arrangement, the base station 2 charges the battery 75 of the console 1 to allow operation of the electrical and mechanical components of the console 1 for a period of greater than approximately one hour.

As indicated above, in the thermal delivery system 150, the console 1 is detachable from the thermal regulation source 158. The configuration of the thermal delivery system 150 decouples or separates the refrigerator from the fluid delivery portion of the console 1 by orienting the thermal regulation source 158 within the base station 2, separate from the console 1. Orientation of the thermal regulation source 158 within the base station 2 allows the console 1 to be thermally charged and separated from the thermal regulation source 158. Such a configuration minimizes the weight of the console 1 and providing ease of transport of the console 1 to a patient location.

FIGS. 1 and 2 illustrate the body-cooling device 152 connected to the thermal delivery system 150. When placed in contact with a patient, the body-cooling device 152, in conjunction with the console 1, manipulates the body temperature of the patient to induce hypothermia in a patient suffering cardiac arrest, acute myocardial infarction, brain trauma, embolic or hemorrhagic stroke, subarachnoid hemorrhage, hemorrhagic shock. For example, the console 1 and body-cooling device 152 induce protective levels of hypothermia within the patient's brain to minimize ischemic injury in the patient. FIGS. 3 through 6, illustrate example configurations of the body-cooling device 152.

Figure 3:
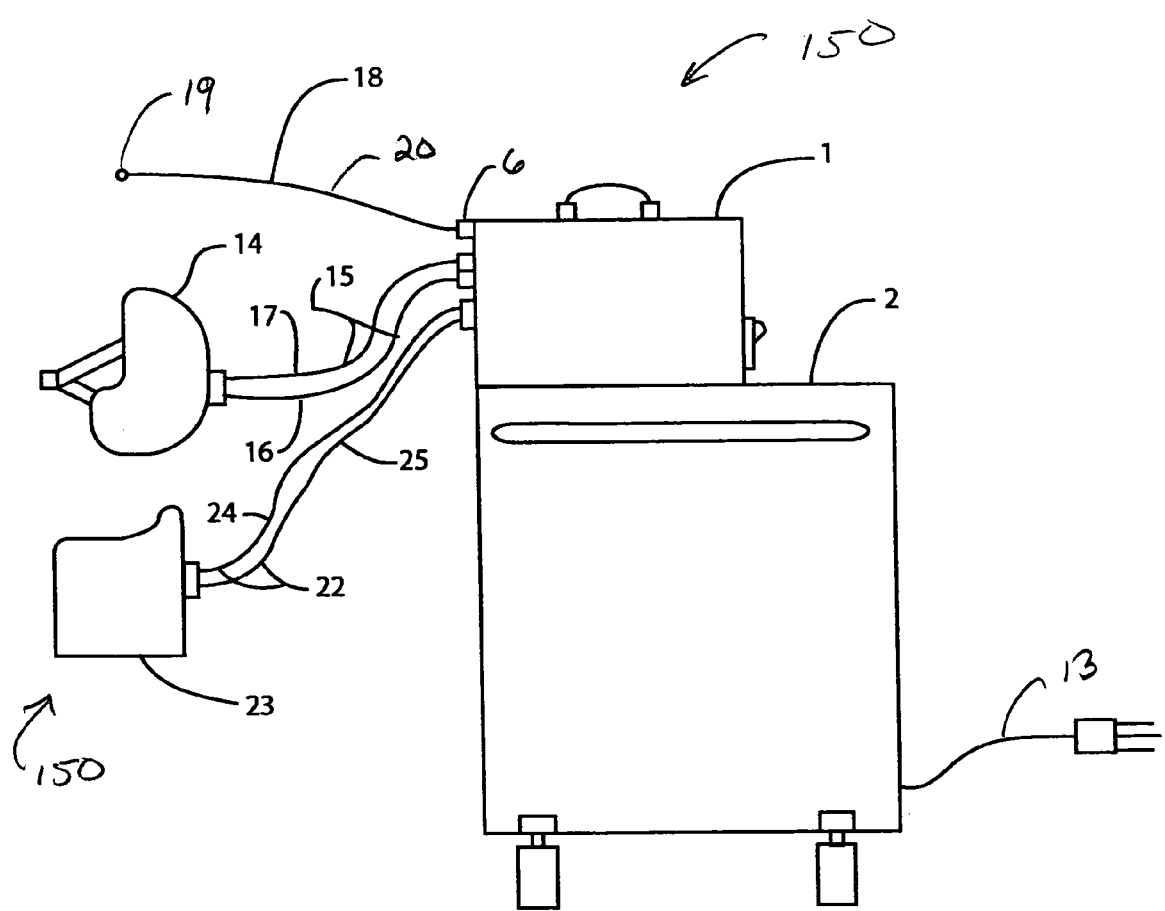
FIG. 3 illustrates a thermal delivery system having an attached head-cooling device, a second body-cooling device and a temperature sensor, according to one embodiment of the invention.

FIG. 3 depicts the console 1, docked with the base station 2, and a head-cooling device 14 removably connected to the console 1 by an umbilical 15. The umbilical 15 includes a cooling fluid infusion tube 16 for delivering fluid to the head-cooling device 14 and a cooling fluid return tube 17 for returning fluid from the head-cooling device 14 to the console 1. The console 1 also includes a neck-cooling device 23 removably connected to the console 1 by an umbilical 22. In one arrangement, the neck-cooling device is configured to thermally contact and cool a patient's neck area (e.g., an area in proximity to the patient's carotid arteries). In another arrangement, the neck-cooling device 23 is configured to thermally contact and cool either the patient's shoulder area or the patient's clavicle area. The umbilical 15 includes a cooling fluid inlet tube 24 for delivering fluid to the neck-cooling device 14 and a cooling fluid outlet tube 25 for returning fluid from the neck-cooling device 14 to the console 1.

A body temperature sensor assembly 18 having a temperature sensor 19 and temperature sensor umbilical 20 removably connects to the console 1 at temperature sensor receptacle. In one arrangement, the temperature sensor 18 is configured to be placed on (e.g., externally contact) or inserted within a patient. For example, in such an arrangement, the body temperature sensor 19 is configured as a Foley catheter, an esophageal catheter, a rectal probe, a tympanic temperature sensor, or a scalp temperature sensor. In another arrangement, the temperature sensor 18 is configured to measure a patient's temperature while minimizing physical patient contact with the temperature sensor. For example, in such an arrangement, the temperature sensor is configured as a magnetic resonance imaging (MRI) device.

During operation, the console 1 supplies cold fluid to the head-cooling device 14 and neck-cooling device 23 under positive gage pressure and removes or scavenges cooling fluid from head-cooling device 14 and neck-cooling device 23 to form a closed loop fluid circulation system. As the fluid travels from the console 1 to the body cooling-device 152 (e.g., head-cooling device 14 and neck-cooling device 23) the temperature of the fluid increases. In one arrangement, after the console 1 receives (e.g., scavenges) the fluid from the head-cooling device 14 and neck-cooling device 23, the console 1 reduces the temperature of the scavenged fluid. For example, when the console 1 docks with the base station, the thermal regulation source 158 and base station thermal conductor 156 provide continuous cooling (e.g., thermal exchange) to the console thermal conductor 154 to maintain the temperature of the fluid within the reservoir 53 at a constant level, such as a temperature near approximately 0° C.

In one arrangement, the console 1 allows the user to select a rate at which the patient's body is cooled (e.g., at the beginning of a treatment) or re-warmed (e.g., toward the end of a treatment). In one arrangement, the console 2 allows a user to select (e.g., set) a predetermined body temperature prior to the initiation of therapy or during therapy. For example, using the control panel 4 of the console, the user programs into a memory (e.g., computer memory) associated with the console 1 a target temperature of the patient. Based upon a feedback loop created between the body temperature sensor 19 (e.g., as placed on the patient) and the console 1 and based upon the target temperature stored in the console's memory, the console 1 automatically adjusts the amount or rate of delivery of the cooling fluid to the patient.

For example, as the console 1 delivers cooling fluid to the body-cooling device 152 (e.g., the head-cooling device 14 and the neck cooling device 23), the console 1 receives a signal from the temperature sensor 19 indicating a temperature of the patient, either local or systemic. The console 1 utilizes the signal from the temperature sensor 19 to control the delivery of cooling-fluid to the body-cooling device 152. For example, assume the signal from the temperature sensor 19 indicates that the patient's body temperature has reached a predetermined temperature. In such a case, the console 1 enters a temperature maintenance mode of operation to provide either an intermittent flow of cooling fluid to the body-cooling device or a continuous flow of cooling fluid to the body-cooling device at a preset rate to maintain the patient's body temperature at the predetermined temperature.

In one arrangement, the console 1 operates the head-cooling device 14 and the neck-cooling device 23, either simultaneously or independently, when the console 1 de-docks from the base station 2. For example, when a user detaches the console 1 from the base station and activates the console at a patient site (e.g., at a location remote from the base station 2), the battery 75 (e.g., a charged battery) provides power to the pump 60 and allows the pump to circulate cooling fluid from the reservoir 53 to the head-cooling device 14 and neck-cooling device 23. In another arrangement, the console 1 operates the head-cooling device 14 and the neck-cooling device 23, either simultaneously or independently, when the console 1 while docked with base station 2 independent of the status of the battery 75 (e.g., whether charged or uncharged) contained within console 1.

Figure 4:
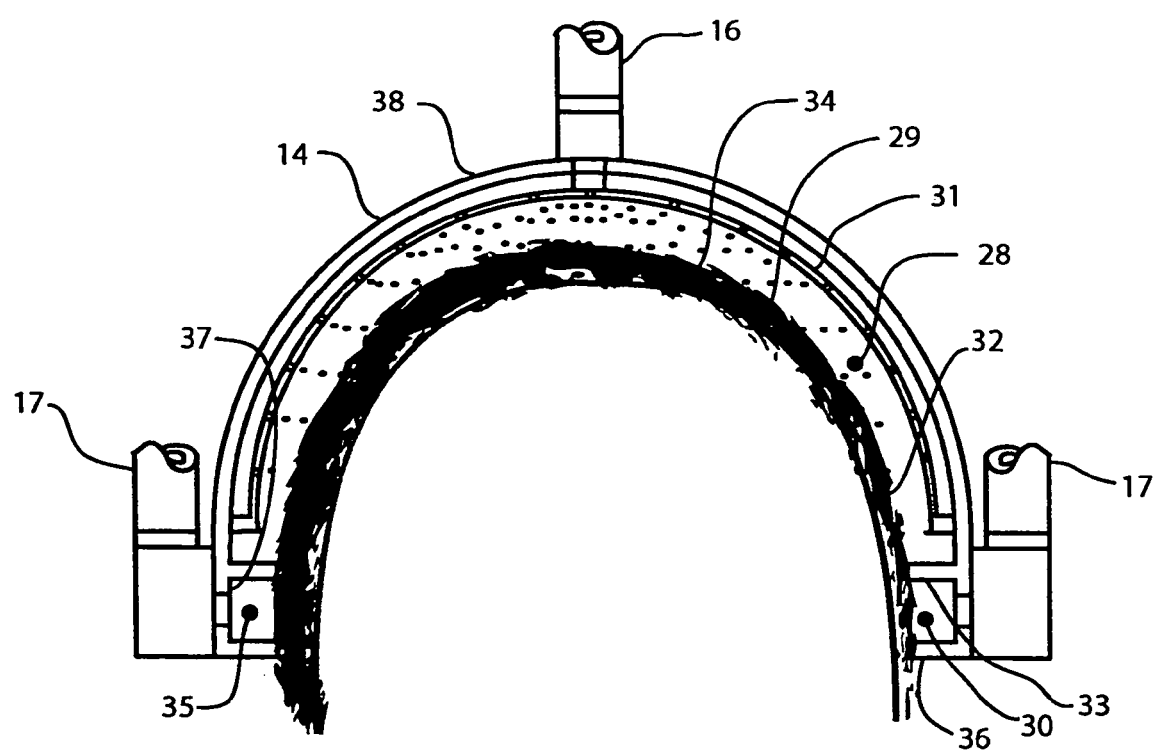
FIG. 4 depicts an arrangement of the head-cooling device of FIG. 3, according to one embodiment of the invention.

FIG. 4 depicts, in sectional view, an example of a head-cooling device 14 used in conjunction with the thermal delivery system 150. The head-cooling device 14 mounts on the head of a patient 29 and defines a cooling fluid circulation space 28, a cooling fluid aspiration space 30, and shows the functional relationship between the cooling fluid circulation space 28 and the cooling fluid aspiration space 30. In one arrangement, the console 1 operates to deliver cooling fluid from the reservoir 53 to the cooling fluid circulation space 28 and to remove fluid from the cooling fluid aspiration space 30.

The cooling fluid circulation space 28 includes the volumetric space between inner wall 31, patient's scalp 32, and inner seal 33, and includes the volumetric space occupied by the patent's hair 34 within the just defined cooling fluid circulation space 30. The cooling fluid aspiration space 30 includes the volumetric space between the patient's scalp 32 and within aspiration channel 35 comprising inner seal 33, outer seal 36 and outer wall 37. The aspiration channel 35 is molded from an elastomer material such as silicone rubber, for example. The aspiration channel 35 defines the entire circumference of the bottom edge of head cap 38 of the head-cooling device 14, as shown. The aspiration channel 35 is sized such that the inner diameter of aspiration channel 35, as defined by the inner diameter of inner seal 33 and/or outer seal 37, is approximately 10 to 30 percent smaller than the circumference of the patient's head 29. Since the circumference of the aspiration channel 35 is smaller than the patient's head 29, when the head cap 38 is placed on the patient's head 29, the inner seal 33, and the outer seal 36 will contact the patient's scalp 32 with a force proportional to the difference in circumference between that aspiration channel 35 and the patient's head 29.

The inner seal 33 is configured by geometry and material selection to resist the flow of fluid from fluid circulation space 28 through the hair 34 into fluid aspiration space 30 such that cooling fluid in fluid circulation space 28 remains at a positive gage pressure between approximately 0.1 and 10 PSI with a fluid flow into head cap 38 of between 0.1 and 1.0 gallons per minute. The outer seal 36 is configured by geometry and material selection to resist the flow of air through the hair 34 from outside head cap 38 into aspiration channel 35 such that pressure within aspiration channel is maintained at a negative gage pressure between −0.1 and −10 PSI by the pump 60 provided by the console 1. Cooling fluid is scavenged completely from the head cap 38 and returned to console 1 provided that the pressure within aspiration channel 35 remains at a negative gage pressure.

The head-cooling device 14 is configured to directing substantially evenly distributed jets of saline or water at near 0° C. at the scalp of a patient in a vigorous manner within the circulation space 28 under positive gage pressure. Such a configuration can effectively induce hypothermia in the patient regardless of the amount of hair on the head, or its distribution on the head. In such an arrangement, the effectiveness the head-cooling device 14 is not substantially affected by the thickness or distribution of the hair on the head, face, or neck of the patient.

Figure 5:
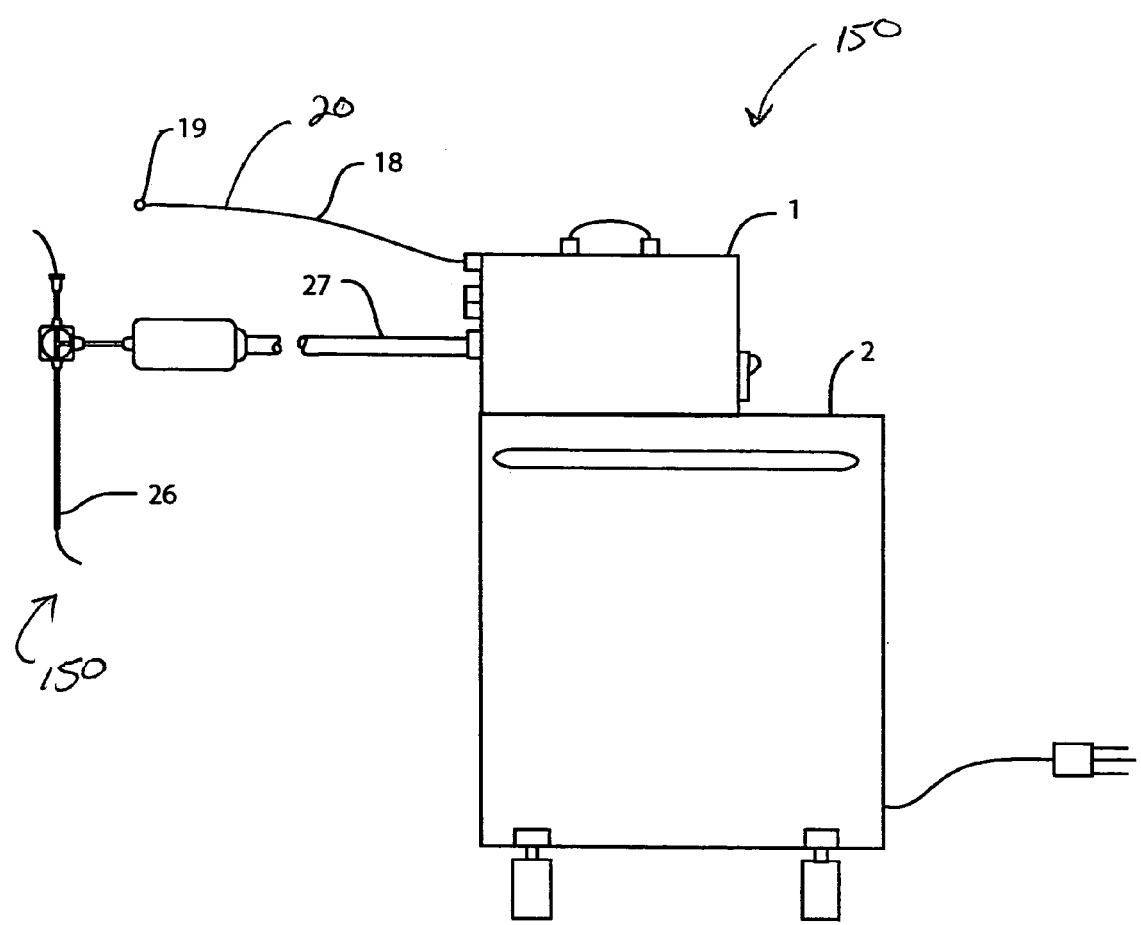
FIG. 5 illustrates a thermal delivery system having an attached blood-cooling device, according to one embodiment of the invention.

FIG. 5 depicts the console 1, docked with the base station 2, and a blood-cooling device 26 removably connected to the console 1 by a blood-cooling device umbilical 27. In one arrangement, the console 1 operates the blood-cooling device 26 via the battery 75 when separated from the base station 2. In another arrangement, the console 1 operates the blood-cooling device 26 while docked with base station 2 independent of the status of the battery 75 (e.g., whether charged or uncharged).

Figure 6:
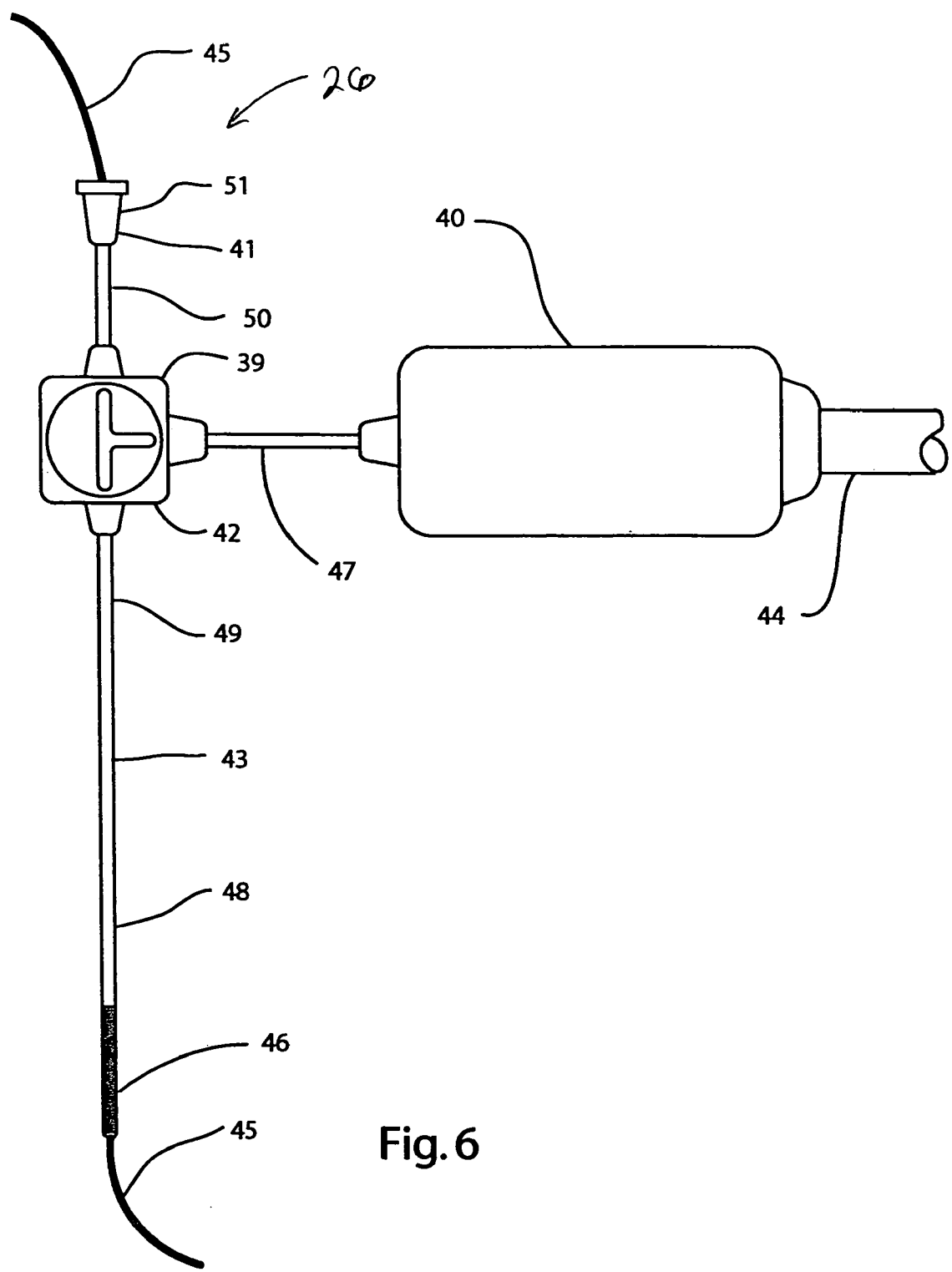
FIG. 6 illustrates an arrangement of the blood-cooling catheter, according to one embodiment of the invention.

FIG. 6 depicts an example of the blood-cooling device 26 of FIG. 5. The blood cooling device 26 includes, for example, a single lumen vascular catheter 39, an ex vivo heat exchanger/pump assembly 40, vascular access port 41, stopcock 42, catheter shaft 43, umbilical 44, guidewire 45, emboli screen 46, and heat exchanger tube 47.

A distal end 48 of the vascular catheter 39 is configured to insert into a major blood vessel of a patient using a guidewire 45 by well-known surgical technique. Typically, the distal end 48 of vascular catheter 39 would be placed through a puncture in the neck of the patient into a jugular vein and the superior vena cava, or into a carotid artery, however, a particular clinical situation may dictate that vascular catheter 39 be inserted into another major blood vessel. When positioned for operation, the distal end 48 resides in vivo in a major blood vessel and a proximal end 49 of the vascular catheter 39 remains ex vivo.

The catheter shaft 43 includes a single lumen and has an inner diameter between approximately 1 mm and 4 mm in diameter, and has a wall thickness between approximately 0.25 mm and approximately 1.0 mm. Catheter shaft 43 can be extruded from common catheter materials such as nylon, polyethylene, or urethane. Glass fiber or metal wire reinforcement may be incorporated into the walls of catheter shaft 43 to provide resistance to kinking or to provide torsional rigidity by means well known to those skilled in the art of catheter design and construction. The catheter shaft 43 is between approximately 10 cm and 20 cm long.

An emboli screen 46 can be incorporated into distal end 48 to provide protection against emboli from leaving vascular catheter 39 and entering the patient's blood stream. Emboli screen 46, for example, includes a woven mesh of fine stainless steel wire with interstice between approximately 250 and 1250 microns, or a multiple of perforations in the wall of catheter shaft 43 of between 250 and 1250 microns, and allows blood to flow into and out of catheter shaft 43 while capturing any emboli or clot that forms inside vascular catheter 39.

The vascular access port 41 includes a vascular access port tube 50 and female luer fitting 51. The vascular access port tube 50 has an inner diameter of approximately 2 mm in diameter and an outside diameter of approximately 3 mm in diameter and is approximately 5 cm to 10 cm long. The vascular access tube 50 may be extruded from a variety of medical grade polymers including nylon and polyethylene. The female luer fitting 51 provides for a standardized connection between a variety of standardized medical sensors such as pressure monitors, blood gas analyzers, and a means of connecting standardized fluid apparatus to the vascular access port including blood bags, IV bags, infusion pumps, and syringes.

The stopcock 42 provides four-way fluid communication between vascular access port 41, catheter shaft 43 and heat exchanger/pump assembly 40. A t-shaped actuator knob 52 is graphically indicative of the fluid path through stopcock 42. With the stopcock 42 positioned as shown there is a fluid communication between vascular access port 41, catheter shaft 43 and heat exchanger/pump assembly 40. With the stopcock 42 positioned 90 degrees clockwise of position shown there is fluid communication between heat exchanger/pump assembly 40 and catheter shaft 43. With the stopcock 42 positioned 180 degrees clockwise of position shown there is fluid communication between vascular access port 41 and catheter shaft 43. With the stopcock 4 positioned 270 degrees clockwise of position shown there is fluid communication between heat exchanger/pump assembly 40 and vascular access port 41. The stopcock 42 is of normal construction for medical device stopcocks and is commercially available from many vendors.

The heat exchanger tube 47 has an inner diameter between 1 mm and 4 mm in diameter and is 5 cm and 10 cm long, and may extruded from various medical grade polymers including nylon and polyethylene. The heat exchanger/pump assembly 40 includes a heat exchanger, a blood pump, and a sensor module (not shown). The umbilical 44 includes at least two secondary heat exchange fluid conduits, and in one embodiment two pump actuating fluid conduits, and a connector between the vascular catheter 39 and the console 1, as illustrated in FIG. 4.

Returning to FIG. 6, during operation, for example, a user places the distal end 48 of vascular catheter 39 is placed into a major blood vessel of a patient using an access needle (not shown) and guidewire 45 by standard surgical technique. The vascular catheter 39 is then secured to the patient with a suture and retaining straps (not shown). The guidewire 45 is removed from vascular catheter 39. The stopcock 42 is then positioned 180 degrees from position shown, a syringe (not shown) is attached to vascular access port 41, and blood is withdrawn from the patient into the syringe. Next, the stopcock 42 is positioned 270 degrees clockwise from position shown and the system is actuated such that blood is pumped into out of the syringe by heat exchanger/pump assembly 40 until heat exchanger/pump assembly 40 is primed with blood and all air is removed from the fluid path between the syringe and the heat exchanger/pump assembly 40 and within heat exchanger/pump assembly 40. The stopcock 42 is then positioned 90 degrees clockwise from position shown which is the operational position. The exchanger/pump assembly 40 withdraws blood from the patient through catheter shaft 43 into heat exchanger/pump assembly 40 where the blood is cooled.

During cooling, the console 1 circulates cooled fluid from the reservoir 53 to the heat exchanger/pump assembly 40 to reduce the temperature of the blood within the exchanger/pump assembly 40. The heat exchanger/pump assembly 40 returns the cooled blood back into the patient through catheter shaft 43 in a cyclical manner where blood is removed from and then reinserted back into the patient at a rate of between approximately 50 and 800 ml/min. During operation, the temperature of the blood can reach between approximately 1° C. and 35° C. within heat exchanger/pump assembly 40. The amount of heat removed from the patient is determined by the flow rate of the blood passing through the heat exchanger/pump assembly 40 and the change in temperature of the blood within the heat exchanger/pump assembly 40.

Figure 7:
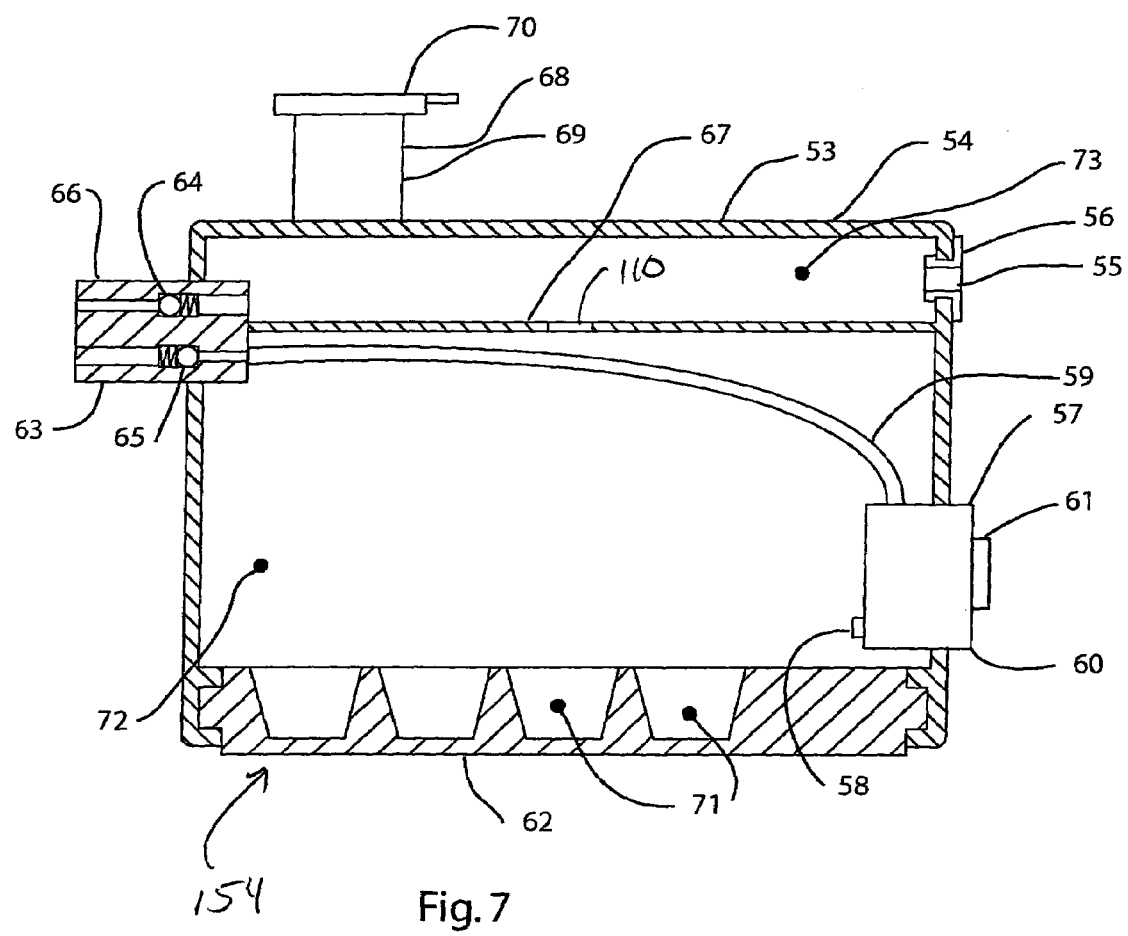
FIG. 7 depicts, in cross sectional view, a removable cassette for use with the thermal delivery system of FIG. 1, according to one embodiment of the invention.

FIG. 7 depicts, in sectional view, an arrangement of the reservoir or cassette 53 of the thermal delivery system 150. The cassette 53 is configured to removably couple to the console 1. In such a configuration, a user can remove the cassette 53 from the console 1 and discard, along with the body-cooling device 152 and all fluid lines (e.g., umbilicals), after use. The use of a removable or disposable cassette 53 allows the user to remove a previously used cassette 53 from the console 1 and insert a sterile cassette with the console 1, prior to operating the console 1, to minimize contamination or infection of a patient. In one arrangement, the cassette 53 is formed from a sanitizable material to allow a user to sanitize and reuse the cassette 53 to minimize contamination or infection of a patient.

The cassette 53 includes a housing 54 having an infusion pump head assembly 57, an umbilical connector assembly 63, a sealable filling port 68, and a console thermal conductor 154. In one arrangement, the housing 54 is formed of a plastic material, such as a thermoplastic or polyethylene material, by a blow molding process. In one arrangement, the wall thickness of plastic housing 54 is approximately 5 mm thick. The umbilical connector assembly 63 and infusion pump head assembly 57, in one arrangement, are ultrasonically welded to plastic housing 54.

Figure 8:
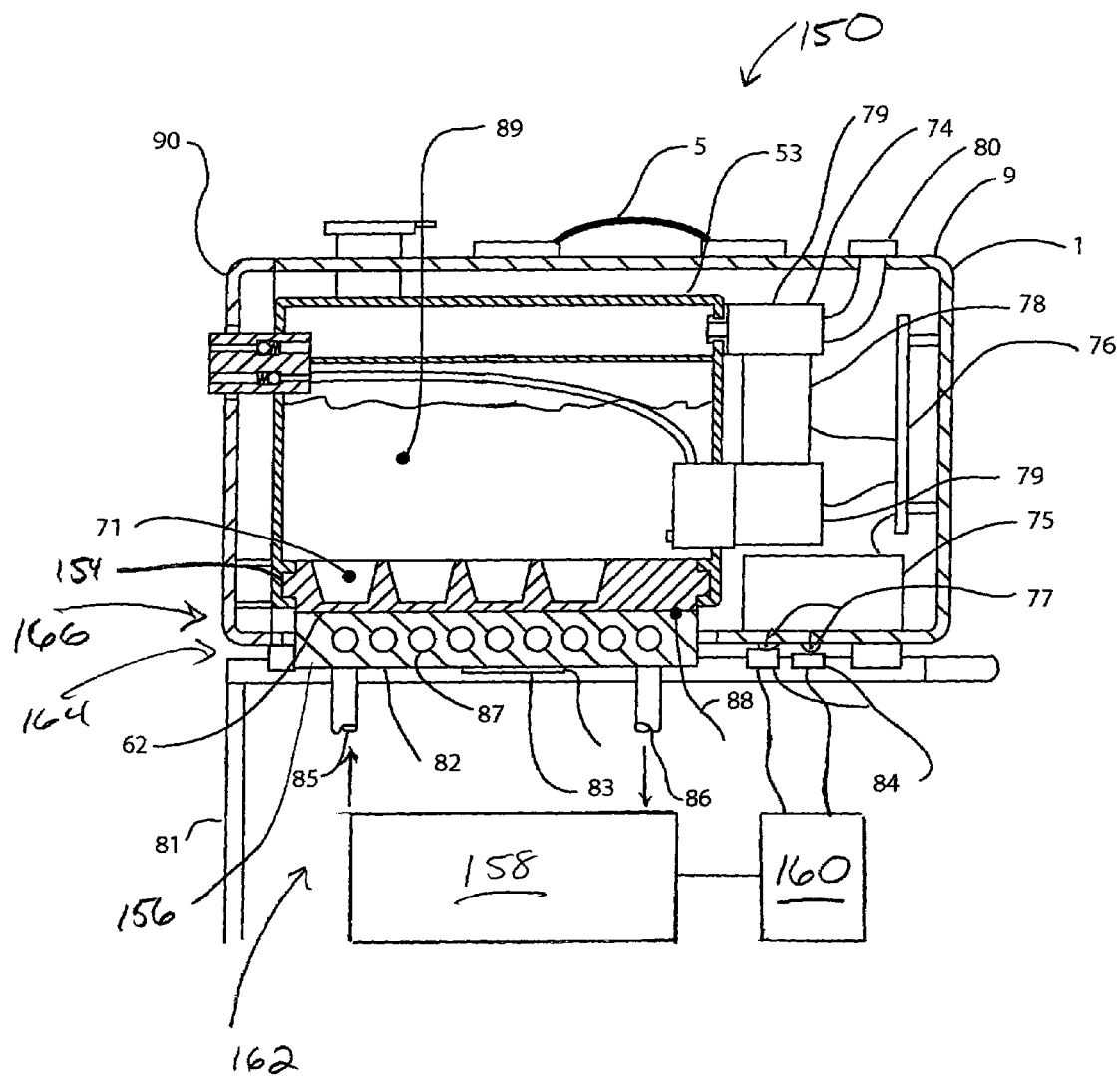
FIG. 8 depicts in cross sectional view the console of FIG. 1 and the functional interface between the console and the base station, according to one embodiment of the invention.

The sealable filling port 68 of the housing 54 includes a user-accessible filler tube 69 and filler tube cap 70 that allows a user to fill or empty the single use cassette 53 with water or ice. The housing 54 defines a fluid reservoir space 72, as shown in the lower section of the cassette 53, and air space 73, as shown in the upper section of the cassette. The housing 54 further defines an aspiration port 55 having an aspiration port grommet 56. The aspiration port 55 provides an air path from the inside of the cassette 53 to an aspiration pump assembly 74 of the console 1, as illustrated in FIG. 8, to place the interior of single use cassette 53 at a negative gage pressure between approximately −0.01 and −10.0 PSIG. Such negative gage pressure allows the console 1 to scavenge fluid from the body-cooling device 152. The aspiration grommet provides a substantially air-tight seal between the use cassette 53 and aspiration pump assembly 74, as illustrated in FIG. 8. In one arrangement the housing 54 includes a divider 67 that forms a boundary between the fluid reservoir space 72 and the air space 73. The divider 67 minimizes fluid (e.g., water or saline) from entering (e.g., splashing) into the aspiration port 55. The divider 67 further defines an opening 110 that allows gas transfer between the fluid reservoir space 72 and the air space 73 to maintain pressure equilibrium between the fluid reservoir space 72 and the air space 73.

Returning to FIG. 7, the infusion pump head assembly 57 includes a fluid inlet port 58, a fluid outlet tube 59, a pump head 60, and a pump motor coupling 61. The infusion pump head assembly 57 transmits fluid (e.g., cold water or saline) within the reservoir 53 under a positive gage pressure between approximately 0.1 and 15 PSIG. During operation, the pump 60 draws fluid, held within the fluid reservoir space 72, into the infusion pump assembly 57 through the fluid inlet port 58. The pump head 60 is configured as a diaphragm, vane, centrifugal or positive displacement pump, for example. As illustrated in FIG. 8, a pump motor 79 drives or operates the pump head 60 via motor coupling 61. In one arrangement, the motor coupling 61 is configured as a magnetic type of motor coupling. During operation, the pump head 60 pressurizes the fluid when driven by pump motor 79 to between approximately 0.1 and 15 PSIG. The pressurized fluid is then delivered to the umbilical connector assembly 63 by fluid outlet tube 59.

The umbilical connector assembly 63 includes an inlet check valve 64, outlet check valve 65, and connector housing 66. The umbilical connector assembly 63 allows connection of an umbilical of a body-cooling device 152, such as umbilical 15, to the cassette 53 and console 1. The umbilical connector assembly 63, in one arrangement, provides fluid communication between the cooling fluid inlet tube 16 of the head-cooling device 14 and the fluid outlet tube 57. The umbilical connector assembly 63, in one arrangement, provides fluid communication between the cooling fluid return tube 17 of the head-cooling device 14 and the air space 73 of single use cassette 53. The umbilical connector assembly 63 is accessible to a user when the single use cassette 53 is in operational position within the console 1.

The console thermal conductor 154, in one arrangement, is configured as an ice cube forming plate 62 having ice cube forming cavities 71. The ice cube forming plate 62 defines a portion of the fluid reservoir space 72 and forms ice cubes in the ice cube forming cavities 71 when docked with base station 2, as illustrated in FIG. 8. The ice cube forming plate 62 is configured as a thermally conductive material, such as a metal. In one arrangement, the ice cube forming plate 62 if formed from an aluminum material plated with a second metal to prevent corrosion. As indicated above, the reservoir 53 and console thermal conductor 154 form a thermal battery. When the thermal battery is fully "charged", the cassette 53 contains a ratio of ice, fluid, and air. For example, in one arrangement, when the thermal battery is fully "charged", the cassette 53 includes approximately 2.5 liters of water or saline in a solid phase (ice), 1.5 liters of water or saline in a liquid phase, and 1 liter of air.

FIG. 8 depicts, in cross sectional view, the functional components of the console 1 and the base station 2 of the thermal delivery system 150, as well as the operational relationship between the console 1 and the base station 2.

The console 1 includes the housing 9, handle 5, a cassette 53, aspiration pump 74 having an aspiration pump head 79, aspiration pump motor 78, and aspiration pump exhaust tube 80, an electrical battery 75, circuit board 76, and electrical contacts 77. The cassette 53 inserts within or removes from the console 1 via a cassette access 90, such as a hinged door formed from the front panel of the console 1 (e.g., shown in the closed position). The console 1 includes an electrical battery 75, a thermal battery, and mechanical and electrical components for operating the console 1 and body cooling device 152 using the internal electrical battery 75 and the internal thermal battery.

The base station 2 includes a base station housing 81, the thermal charging assembly 162 and a power source 160 electrically coupled to electrical contacts 84. The base station thermal conductor 156 of the thermal charging assembly 162 is configured, in one arrangement as a thermal battery charging plate 82 defining fluid conduits 87, fluid inlet tube 85, fluid outlet tube 86, a transducer 83, and a temperature sensor 88. The thermal regulation device of the thermal charging assembly 162, in one arrangement, is a refrigeration device that circulates fluid through the fluid inlet tube 85, the fluid conduit 87 within thermal battery charging plate 82, and fluid outlet tube 86.

The console 1 and base station 2 are constructed with a mutual docking assembly 164. The docking assembly 164 allows a user to couple the console 1 to the base station 2 to charge either the thermal battery of the console 1, the electrical battery 75 of the console 1, or both. For example, in one arrangement, the docking assembly 164 includes a thermal contact location between the thermal battery charging plate 82 of the base station 2 and the ice cube forming plate 62 of the single use cassette 53. In another arrangement, the docking assembly 164 includes an electrical contact location between the electrical contacts 77 of the console 1 and the electrical contacts 84 of base station 2.

As indicated above, a user docks the console 1 with the base station 2 to allow the base station to thermally alter (e.g. reduce the temperature of) fluid within the cassette 53 of the console and electrically charge the battery 75 of the console 1. Such thermal and electrical charging allows the user to disconnect the console 1 from the base station 2, transport to a patient location (e.g., a pre-hospital setting), and operate an associated body-cooling device 152 to induce localized hypothermia in the patient. The following description outlines an example operational relationship between the base station 2 and console 1 to thermally charge or form ice within single use cassette 53 of console 1.

Initially, a user docks the console 1 with the base station 2 to engage the mutual docking assembly 164. In one arrangement, the circuit board 76 is configured to control operation of the base station 2 when the console 1 docks with the base station 2. For example, as the electrical contacts 77 of the console 1 engage the electrical contacts 84 of the base station 2, the console 1 activates the base station 2 to an operational or "on" mode. The circuit board 76 then exchanges electrical control signals with the base station 2 to control the operation of the base station 2 according to the state of the electrical battery 77, the state of the thermal battery within the console 1, or the state of operation of the console 1.

After the user docks the console 1 with the base station 2, the base station 2 charges the electrical battery 75 of the console 1 via the power supply 160. By charging the battery 75, the power supply 160 allows the console 1 to operate while detached from the base station 2 for a certain duration of time (e.g. a period between approximately one and four hours). Electrical contacts 84 of the base station 2 electrically couple to the power supply 160 and form an electrical connection with electrical contacts 77 of the console 1. Docking of the console 1 with the base station 2 provides an electrical connection between the base station 2 and the console 1 to charge the electrical battery 75 of console 1.

The user adds fluid, such as water or saline, to single use cassette 53 through sealable filling port 68. The base station 2 engages an ice-forming mode of operation where the thermal regulation source 158 circulates a relatively low temperature fluid through the conduits 87 located within the thermal battery charging plate 82. Such circulation reduces the temperature of the thermal battery charging plate 82 and, in turn, the ice cube forming plate 62, to a temperature substantially below 0° C. (e.g., between the range of approximately −5° C. to −40° C.).

During the ice-forming mode of operation, the ice forming is monitored by a transducer or sensor 83. In one arrangement, the transducer 83 is an ultrasound transducer. The sensor 83, for example, monitors ice formation in the ice cube forming cavities 71 of ice cube plate 62 of the single use cassette 53. The sensor 83, in conjunction with a signal processor (e.g., the circuit board 76 of the console 1 or circuitry of the base station), also detects the volume of fluid within the cassette 53 that is in a frozen state.

When ice cubes are fully formed in ice cube cavities 71 of ice cube forming plate 62, as determined by transducer 83, an ice release mode of operation is initiated by the thermal delivery system 150. In such a mode of operation, the thermal delivery system 150 activates a heating element 166 to cause the thermal battery charging plate 82 and ice cube forming plate 62 of the single use cassette 53 to obtain a temperature above 0° C. in a relatively short period of time. As such, the heating element 166 causes the ice within the ice-forming cavities 71 to partially melt thereby resulting in the ice cubes releasing from the cavities 71 and floating to the surface of water or saline 89. In one arrangement, the base station thermal conductor 156 is configured as the heating element 166. In such an arrangement, the base station 2 circulates a fluid having a temperature above 0° C. through the conduit 87 of the thermal battery charging plate 82. The thermal battery charging plate 82 transfers the heat from the fluid to the ice cube forming plate 62. In another arrangement, the heating element 166 is configured as an electrical heater in thermal communication with the console thermal conductor. Once ice cube release is completed, as determined by the transducer 83, the base station 2 reinitiates and re-engages the ice-forming mode of operation.

The sensor 83 and heating element 166 work in conjunction with each other to repeat the ice forming and releasing cycles until the volume of water or saline 89 in a frozen state reaches a predetermined volume, as determined by transducer 83. For example, the base station repeats the cycle until the cassette 53 includes approximately 2.5 liters of water or saline in a solid phase (ice) and 1.5 liters of water or saline in a liquid phase. When the volume of water or saline 89 in a frozen state falls below the predetermined volume, the ice-forming mode of operation is then reinitiated thereby maintaining a full thermal charge of the thermal battery. In such an arrangement, the sensor 83 and heating element 166 work in conjunction with each other to reduce the temperature of the fluid within the reservoir 53 to a preset temperature (e.g., a temperature of approximately 0° C.) and to maintain the fluid temperature at the preset temperature.

When a user docks the console 1 with the base station 2, the base station 2 thermally charges the console 1 (e.g., reduces the temperature of fluid held by the reservoir 53) and electrically charges the battery 75 of the console. As such, the base station 2 allows the user to decouple or disconnect the console 1 from the base station 2 and operate the console 1, separate from the base station 2, to provide cooling to a patient, via the body-cooling device 152, for a period of greater than 1 hour (e.g., between approximately 1 to 4 hours). Also, as indicated above, the docking station 2 includes a thermal regulation source 158, such as a refrigerator, configured to adjust the temperature of fluid held by the reservoir 53 of the console 1. By locating the thermal regulation source 158 in a location accessible by, but separate from, the console 1 (e.g., not housed within the housing 9 of the console 1), the thermal delivery system 150 effectively reduces the weight of the console 1. As such, the thermal delivery system 150 provides a user with the ability to transport the thermally and electrically charged console 1 to a patient location to induce protective levels of hypothermia within the patient, via the body-cooling device 152.

During operation of the console 1, over time, the temperature of the fluid within the reservoir 53 increases and the power output of the battery 75 decreases. In the case where the temperature of the fluid (e.g., the temperature of the thermal battery) increases beyond a threshold temperature or in the case where the power level of the battery 75 falls below a given threshold, the user disconnects the body-cooling device 152 from the failing or expired console 1 and attaches the body-cooling device 152 to a second console having a charged thermal and electrical battery while the body-cooling device remains attached to the patient in an operational position. Such a procedure allows the user to maintain a hypothermic state in a patient for an extended period of time in a pre-hospital setting (e.g., in a location where the user has no or minimal access to a base station 2).

As indicated above, the console 1 induces protective levels of hypothermia within the patient, via the body-cooling device 152. In one arrangement, the console 1 also includes a treatment apparatus that provides an additional treatment regimen to the patient.

Figure 9:
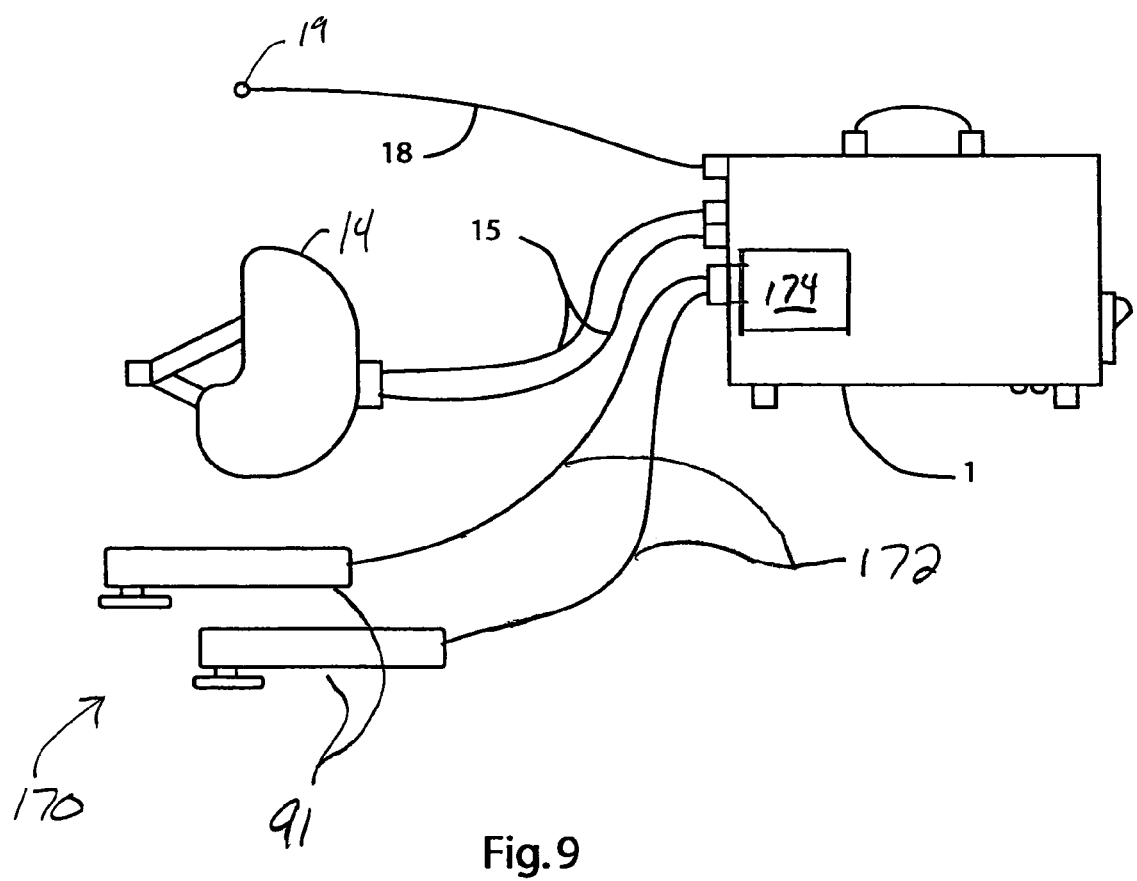
FIG. 9 illustrates an arrangement of the console having a treatment apparatus, according to one embodiment of the invention.

FIG. 9 depicts in simplified form console 1 with head-cooling device 14 attached by umbilical 15, temperature sensor assembly 18 attached, and a treatment apparatus 170 coupled to the console 1. The treatment apparatus 170 includes defibrillator electrode paddles 91 coupled to a defibrillator 174 associated with the console 1 via connectors 172. In one arrangement, the defibrillator 174 automates defibrillation of the patient.

The console 1 of FIG. 9 allows resuscitation of a subject or patient stricken with cardiac arrest. For example, during operation, a user (e.g., medical technician) transports the console 1 to a patient undergoing cardiac arrest. The user applies the defibrillator paddles 91 to the patient, engages the defibrillator 174 of the console 1 (e.g., places the defibrillator in an "on" mode of operation), and defibrillates the patient. The user places the head-cooling device 14 on the patient's head, places the temperature sensor 19 on or into the patient's body, and connects the temperature sensor 19 to the console 1 using the lead 18. The user connects the head-cooling device 14 to the console 1 using the umbilical 15. The user activates the console 1 to provide cooling fluid to the head of the patient to minimize ischemic injury in the patient.

As indicated above, the console 1 docks with the base station 2 to form a thermal delivery system 150 and operates while docked to the base station 2. In one arrangement, the console 1 and base station 2 form part of a resuscitation system or resuscitation apparatus that provides substantially continuous body cooling to a patient, via a body-cooling device 152, and allows for resuscitation of the patient using additional treatment modalities.

Figure 10:
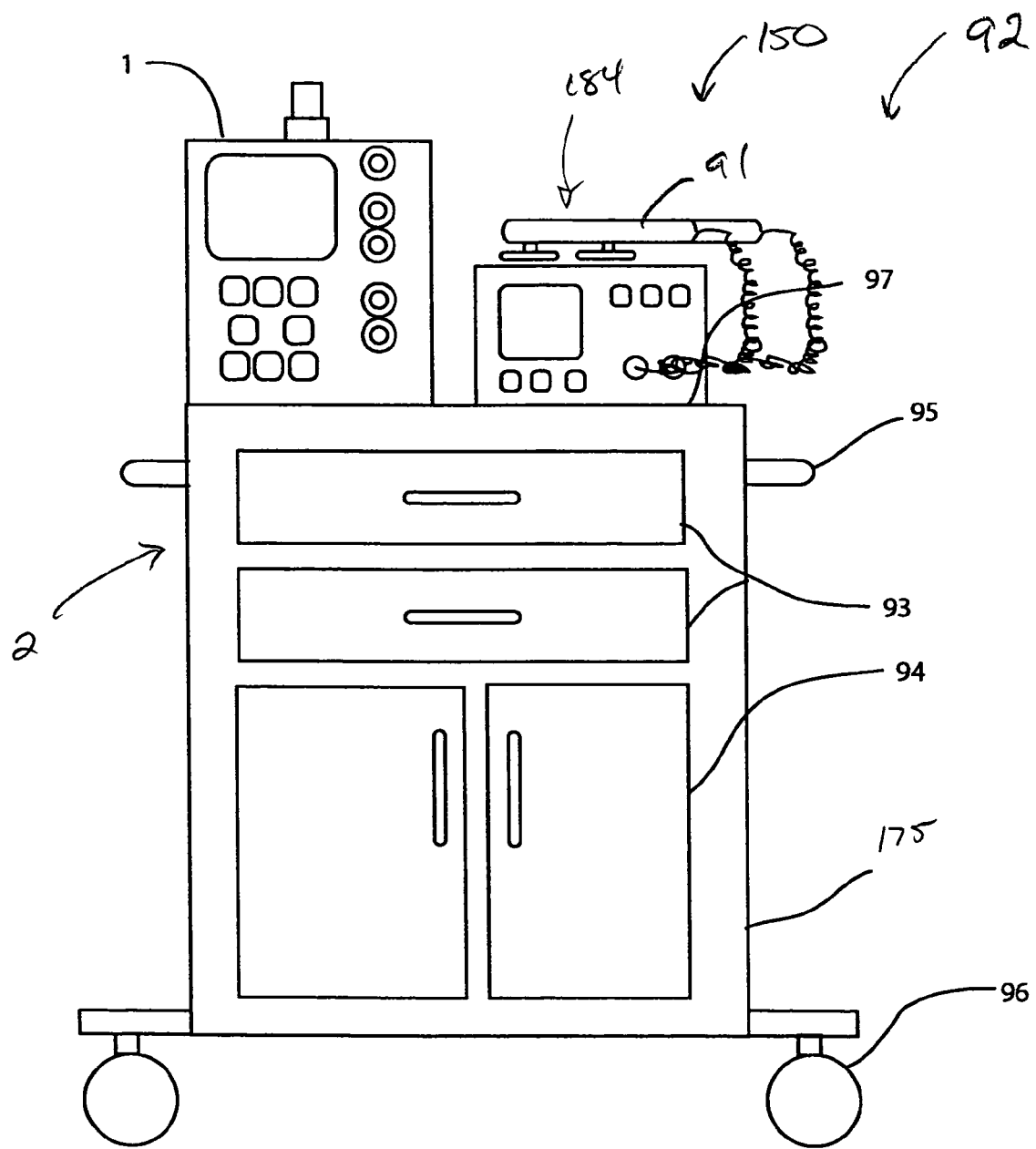
FIG. 10 depicts a crash cart forming a base station for a console, according to one embodiment of the invention.

FIG. 10 illustrates an arrangement of the thermal delivery system 150 configured as a crash cart 92. The crash cart 92 includes a housing 175 having drawers 93 and cabinets 94 for storing resuscitation medications, supplies, and devices. The crash cart 92 also includes handles 95 and wheels 96 to allow transport of the crash cart 92 from a place of storage to a patient in need of resuscitation, and a secure storage space for a defibrillator 97. The crash cart 92 also includes a defibrillation apparatus 184 secured to the crash cart 92 at a coupling location 97, the defibrillation apparatus 184 having a defibrillator 174 and defibrillator electrodes 91.

The crash cart housing 175 holds the base station 2. As described above, the console 1 (e.g., body temperature management system) docks with the base station 2 of the housing 175 to thermally charge (e.g., alter the temperature of the fluid within the reservoir 53) and electrically charge (e.g., provide power to a battery 75 associated with) the console 1.

During operation, a user transports the crash cart 92 to a location of a patient requiring resuscitation. The user induces a hypothermic state within a portion of the patient (e.g., within the patient's brain) using the console 1 and a body-cooling device 152). The user also resuscitated the patient by applying the defibrillation electrodes 91 to the patient and activating the defibrillator 174.

Figure 11:
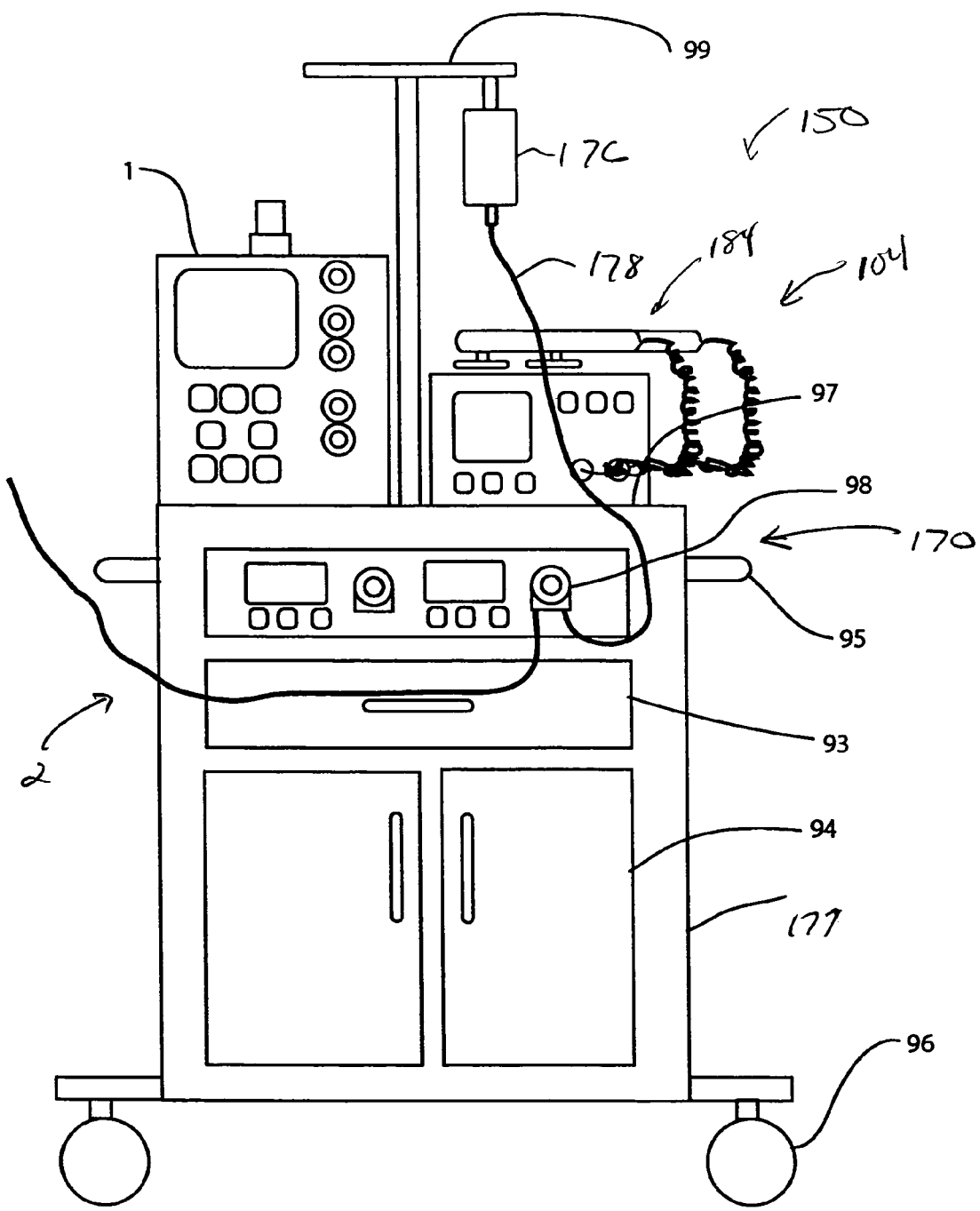
FIG. 11 depicts a trauma resuscitation console forming a base station for a console, according to one embodiment of the invention.

FIG. 11 illustrates an arrangement of the thermal delivery system 150 configured as a trauma resuscitation console 104. The trauma resuscitation console 104 includes a housing 177 having a base station 2, a portable console 1, drawers 93 and cabinets 94 for storing resuscitation medications, supplies and devices, handles 95 and wheels 96 to allow transport of the trauma resuscitation console 104 from a place of storage to a patient in need of resuscitation, and a secure storage location 97 for a defibrillator 184. The resuscitation console 104 also includes a treatment apparatus 170 in the form of a fluid infusion pump 98 that, in one arrangement, provides metered infusion of fluids into the patient.

During operation, a user transports the trauma resuscitation console 104 to a location of a patient requiring resuscitation and operates the console 1, body-cooling device 152 and defibrillator 184, as described above. The user further aids in resuscitating the patient by hanging a fluid bag 176 from a fluid bag hanger 99 of the console 104, feeding a line 178 of the fluid bag 176 through the pump 98 and attaching the line 178 to a patient (e.g., inserts the line into a blood vessel of the patient). The pump 98, in one arrangement delivers the fluid from the fluid bag 176, such as a Ringer's solution, to the patient to maintain a hydration level of the patient. In another arrangement the pump delivers a fluid medicament from the fluid bag 176 to the patient.

Figure 12:
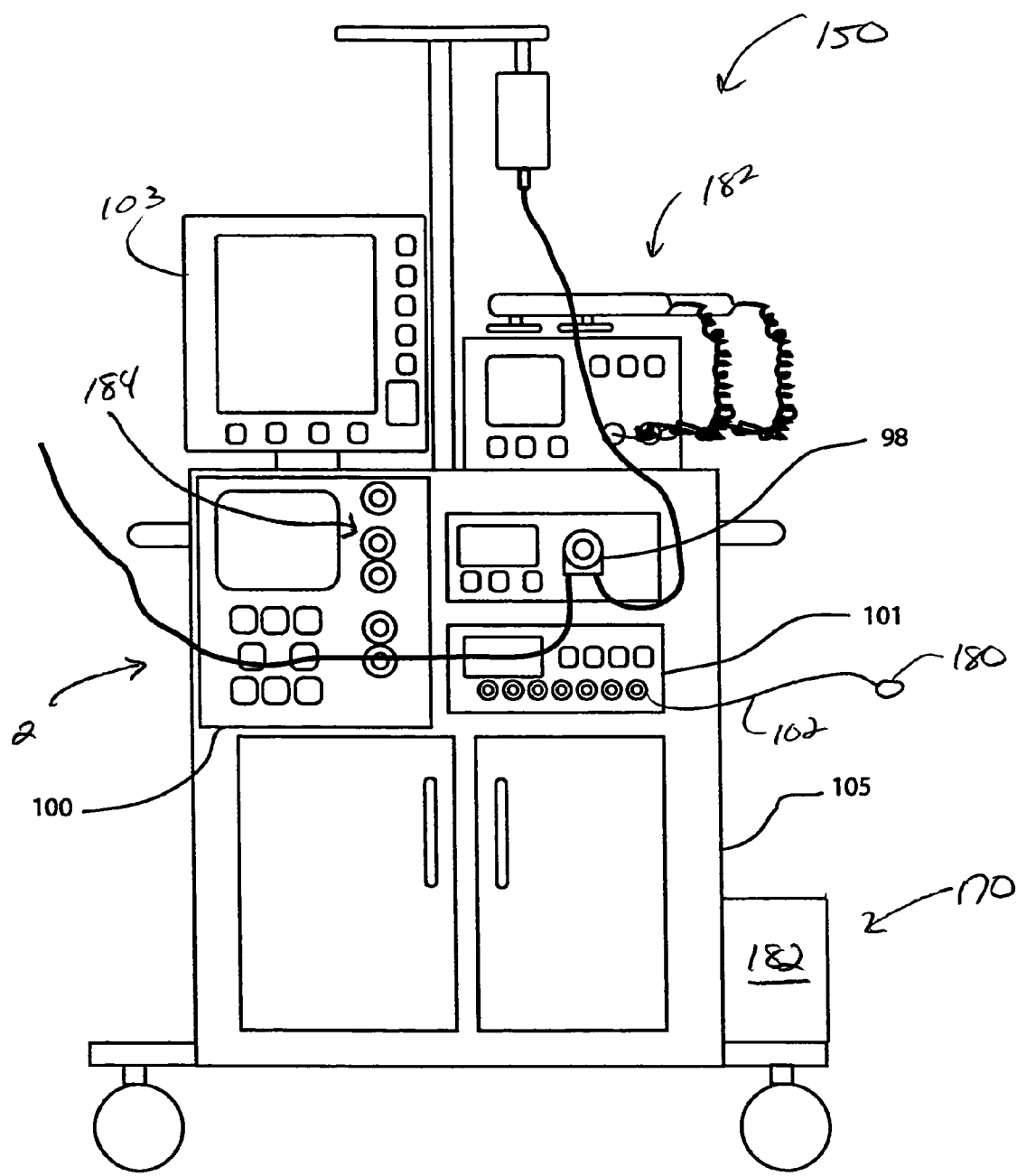
FIG. 12 depicts a life support console, according to one embodiment of the invention.

FIG. 12 illustrates an arrangement of the thermal delivery system 150 configured as a life support system 105. The life support system 105 includes a body temperature management system 100, a physiological monitor 101 connected, via connector 102, to a physiological sensor 180, a fluid infusion pump 98, a defibrillation apparatus 182, and a treatment apparatus 170 configured as a patient ventilator 182. The life support system 105 also includes an integrated control and display panel 103 that operates and controls, in one arrangement, the physiological monitor 101, fluid infusion pump 98, and the patient ventilator 182.

The body temperature management system 100 includes connectors that connect to a body-cooling device 152 via an umbilical. The body temperature management system 100 is configured to lower a patient body temperature to a predetermined level, and maintain the patient's body temperature at the predetermined level for an extended period of time using the body-cooling device 152. In one arrangement, the body temperature management system 100 is configured as a console 1, as described above.

The physiological monitor 180 detects a physiologic state of a patient. For example, the physiological monitor 180 is configured as an electrocardiogram (EKG) sensor, a heart monitoring sensor, a temperature sensor, or a pulse oximetry sensor. The life support system 105 can adjust delivery of cooling fluid from the body temperature management system 100, to adjust or maintain the patient's body temperature of a patient, based upon the signals received from the physiological monitor 180. The ventilator 182 couples to a patient airway and provides oxygen and other gasses to the patient, thereby providing inhalation therapy to the patient and aiding in the resuscitation of the patient.

Regarding the thermal delivery system 150, as indicated above, the console 1 includes a console thermal conductor 154 and the base station 2 includes base station thermal conductor 156 and thermal regulation source 158. When the console 1 docks with the base station 2, the thermal regulation source 158 adjusts or modifies a temperature of the base station thermal conductor 156. The base station thermal conductor 156, in turn, adjusts the temperature of the console thermal conductor 154 to modify (e.g., reduce) the temperature of the fluid within the reservoir 53.

Figure 13:
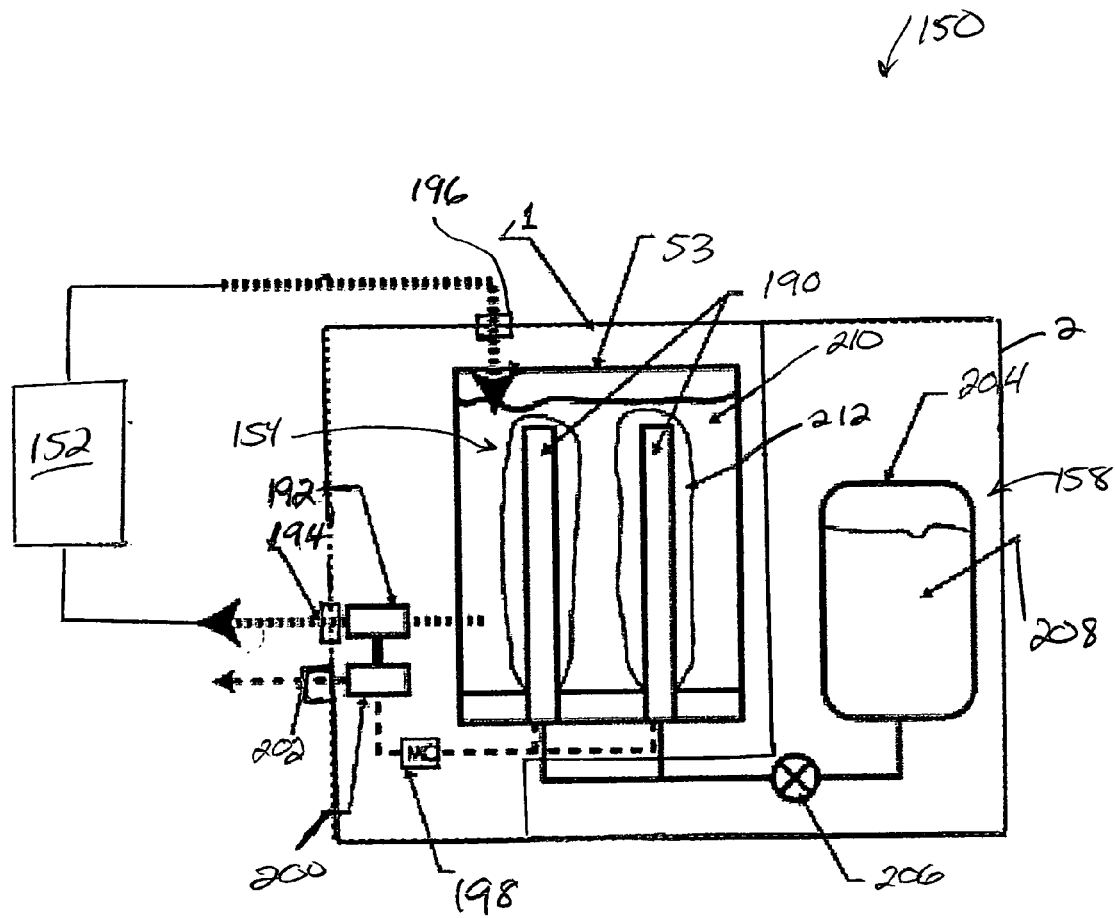
FIG. 13 illustrates an alternate arrangement of a thermal delivery system of FIG. 1, according to one embodiment of the invention.

FIG. 13 illustrates an arrangement of a thermal delivery system 150 that utilizes a liquid gas source and evaporators to reduce the temperature of a fluid held by a reservoir 53 of a console 1.

The console 1 includes a console thermal conductor 154 configured as a liquid gas evaporator 190 oriented in communication with the reservoir 53 of the console 1. The console 1 further includes a fluid outlet 194, a fluid inlet 196 and a pump 192 oriented between the reservoir 53 and the fluid output 194. The console 1 also includes a pressure control valve 198, a gas outlet 202, and a turbine coupled to the gas outlet 202, the pump 192 and the pressure control valve 198.

The base station 2 includes a thermal regulation source 158 configured as a liquid gas source 204, such as a cryogen tank, and a control valve 206 coupled to the liquid gas source 204. The liquid gas source 204 contains a cryogen, such as liquid nitrogen.

During operation, the base station 2 delivers the cryogen (e.g., liquid gas) 208 from the liquid gas source 204 to the evaporators 190 of the console 1. In one arrangement, the base station 2 automatically adjusts the control valve 206 to initiate delivery and regulate delivery (e.g., regulate volume flow rate) of the liquid gas 208 to the evaporators 190. As the liquid gas 208 reaches the evaporators 190, the liquid gas 208 reduces the temperature of the evaporators 190 that, in turn, reduces the temperature of the fluid 210 within the reservoir 53. Over time, due to the evaporation of the liquid gas 208 by the evaporators 190, the evaporators 190 develop an ice layer 212 that aids in maintaining and stabilizing the temperature of the fluid 210 within the reservoir 53 to a temperature of approximately 0° C. The pump 192 circulates the fluid 210 from the reservoir 53, through the fluid outlet 194, through a body-cooling device 152 and back to the reservoir 53 via the fluid inlet 196 to reduce the temperature of the body-cooling device 152.

In one arrangement, as the evaporators 190 convert the cryogen 208 from a liquid to a gaseous state to cool the fluid 210 within the reservoir 53, the evaporators 190 deliver (e.g., exhaust) the gas, through the pressure control valve 206, to the turbine 200. The turbine 200 receives the gas and, in turn, drives the pump 192 to circulate fluid 210 to the body-cooling device 152. Such an arrangement minimizes the necessity for a power source to provide power to the pump 192 to deliver fluid 210 from the reservoir 53 to the body-cooling device 152.

During operation, the turbine 200 exhausts a portion of the gas received from the liquid gas from the evaporators 190 through the gas outlet 202. The gas outlet 202 releases the gas at a pressure greater than ambient pressure. As such the gas can be used to aid in sealing body-cooling device 152, such as a head-cooling device, to a patient's head. For example, assume a head-cooling device is configured with a rim having an inflatable bladder. A user places the head-cooling device on a patient's head and couples a fluid circulation space, defined by the head-cooling device, to the fluid input 196 and fluid output 194 of the console 1. The user then connects the inflatable bladder to the gas outlet 202 of the console 1. During operation, the console 1, via the pump 192, circulates cooling fluid to the patient's scalp within the fluid circulation space to adjust or lower the body temperature of the patient. Also during operation, the console 1, via the turbine 200 and gas outlet 202, delivers gas to the bladder oriented about the rim of the head-cooling device to inflate the bladder and seal the rim of the cap against the patient's head. Such sealing minimizes leakage of the cooling fluid past the rim of the head-cooling device.

Figure 14:
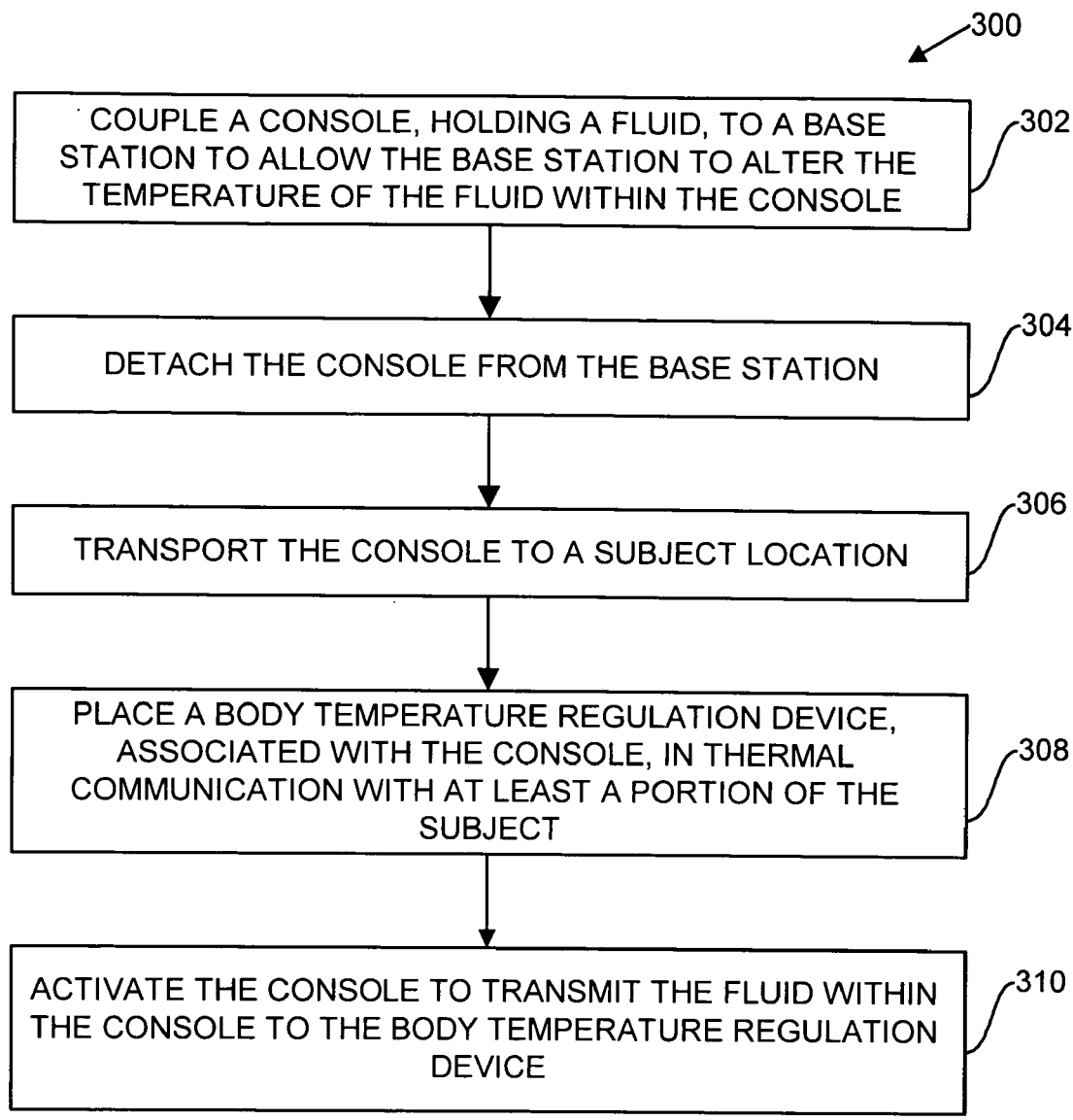
FIG. 14 illustrates a flowchart of a procedure for altering a body temperature of a patient, according to one embodiment of the invention.

FIG. 14 illustrates a flowchart 300 of a procedure for altering a body temperature of a subject (e.g., patient) utilizing the thermal delivery system 150. A health care professional, such as an emergency care technician, can perform the procedure.

In step 302, a user couples a console 1, holding a fluid, to a base station 2 to allow the base station 2 to alter the temperature of the fluid within the console 1. For example, when the console 1 docks with the base station 2, the console thermal conductor 154 of the console 1 thermally couples to the thermal regulation source 158 of the base station 2, via the base station thermal conductor 156. As a result of the docking, the thermal regulation source 158 adjusts the temperature of the console thermal conductor 154 to reduce the temperature of the fluid within reservoir 53 to a preset level (e.g., charge the thermal battery) and continuously maintain the temperature of the fluid at the preset level.

In step 304, the user detaches the console 1 from the base station 2 and, in step 306, transports the console 1 to a subject or patient location. As indicated above, the thermal regulation source 158 orients within the base station 2, separate from the console 1. Such a configuration allows the user to detach the console 1 from the base station 2, (e.g., after charging of the thermal battery of the console 1) and transport the console to a patient location while minimizing the weight of the console 1 and providing ease of transport to the patient location.

In step 308, the user places a body temperature regulation device, associated with the console 1, in thermal communication with at least a portion of the subject and, in step 310, activates the console to transmit the fluid within the console to the body temperature regulation device. In one arrangement, the body temperature regulation device is configured as a body-cooling device 15, such as a head-cooling device, neck-cooling device, or blood-cooling device. The body-cooling device 152, in one arrangement, induces protective levels of hypothermia within the patient's brain to minimize ischemic injury in the patient. In one arrangement, the user also applies some treatment to the patient, using a treatment apparatus, to provide resuscitation to the patient. For example, in the case where the console 1 is configured with a defibrillation apparatus 184, the user defibrillates the patient using associated defibrillation electrodes 91.

After the user has completed thermal therapy (e.g., induction of hypothermia) on the patient, the user can dock the console 1 with a base station 2 to recharge the thermal battery and electrical battery 75 of the console. For example, assume the user de-docks the console 1 from a first base station located at a first hospital and transports the console 1 to a patient location outside of the first hospital. Further assume that while applying thermal therapy to the patient, the user transports the patient to a second hospital. When the user completes thermal therapy on the patient (e.g., as required by a loss of power from the battery 75 or by an increase in temperature of the fluid held by the reservoir 53) the user docks the console 1 with a second base station 2 stored at the second hospital allow the second base station to alter the temperature of the fluid within the console. By having base stations oriented at multiple locations, a user can readily recharge the thermal and electric batteries associated with the console 1 to prepare the console for upcoming emergencies.

While this invention has been particularly shown and described with references to preferred embodiments thereof, it will be understood by those skilled in the art that various changes in form and details may be made therein without departing from the spirit and scope of the invention as defined by the appended claims.

For example, as indicated above, the cassette is configured with a single chamber to hold fluid. In one arrangement, the cassette 53 defines multiple (e.g., two or three distinct) chambers. In such an arrangement, a first chamber is an ice-forming chamber having a fluid conduit that traverses the ice-forming chamber and a second chamber is a fluid reservoir containing water or saline. During operation, the water or saline from the reservoir is circulated through the fluid conduit while ice is present within the ice-forming chamber to therefore cool the water or saline.

As illustrated in FIG. 3, the body-cooling device 152 includes a neck-cooling device 23 for lowering a body temperature of a patient and inducing hypothermia in the patient. Such illustration is by way of example only. In one arrangement, the body-cooling device 152 is configured as a cooling pad to be applied at any physiologic location of the patient.

As indicated above, the base station 2 can be configured as a stand-alone apparatus (e.g., dedicated to thermally and electrically charging a docked console) or as part of an integrated structure (e.g., as part of a crash cart, a trauma resuscitation console, or a life support system), configured for selective placement (e.g., transport) within in a hospital setting. In one arrangement, the base station 2 orients in a fixed location within the hospital, such as by being incorporated into a fixed piece of furniture or mounted on a wall. In another arrangement, the base station 2 is integrated within a structure configured for selective placement (e.g., transport) outside of the hospital setting. For example, in one arrangement, the base station 2 is incorporated into the interior of an ambulance and operated by the either the electrical system of the ambulance or by a dedicated power source within the ambulance, for example. In another arrangement, the base station 2 is incorporated into the interior of an aircraft and operated by either the electrical system of the aircraft or by a dedicated power source within the aircraft, for example. In another arrangement, the base station 2 is configured for deployment in a battlefield environment where the base station includes a self-contained power source, such as an engine and an electric generator.

As indicated above, the console 1 includes an aspiration pump 74 having an aspiration pump head 79, aspiration pump motor 78, and aspiration pump exhaust tube 80. As indicated, the aspiration pump 74 is configured to, in one arrangement, aspirate fluid from a channel 35 of the head-cooling device 14. Such indication is by way of example only. In another arrangement, channel 35 of the head-cooling device couples to an aspiration manifold built into the walls of a hospital or into an ambulance, for example, that aspirates the head-cooling device 14.

In one arrangement, the console 1 is configured to accommodate an assortment of cassette 53 designs whereby the design and construction of the cassette 53 is determined by the specific body-cooling device 152 to be operated by the console 1.

As described above, during operation, the user adds fluid, such as water or saline, to the single use cassette 53 through sealable filling port 68. The base station 2 engages an ice-forming mode of operation where the thermal regulation source 158 circulates a relatively low temperature fluid through the conduits 87 located within the thermal battery charging plate 82 to form ice within the cassette 53. In one arrangement, the user adds ice to the cassette 53 whereby the ice forms the thermal battery of the console 1.

As described above, when a user couples the cassette 53 to the console 1 and attaches the console 1 to the base station 2, the base station 2 reduces the temperature of the fluid within the cassette or reservoir 53 to charge the thermal battery of the console 1. Such description is by way of example only. In another arrangement, the base station is configured to charge the thermal battery within the cassette while the cassette is removed or unattached from the console 1.

As indicated above, the console 1 provides cooling fluid to a patient, via the body-cooling device 152, to induce global or local hypothermia in the patient. In one arrangement, the console 1 provides patient warming, such as by a warming fluid delivered to the patient via the body-cooling device 152. The console 1 also includes a rewarming rate controller that controls the rate at which a patient rewarms from a cooled state.

As described above, the console includes a display panel 3 that provides a user with graphical and alpha/numeric information on the status and operation of the console 1. In one arrangement, the console 1 via the display panel 3 provides the user with information on the state of charge of the thermal battery of the console 1 and/or the state of charge of the electrical battery 75.

As illustrated in FIG. 9, the console 1 includes a defibrillator coupled with the console 1. In one arrangement, the defibrillation is built into the crash cart 92, the resuscitation console 104, or the life support console 105.

As indicated above, the blood-cooling device 26 removes blood from a patient via a catheter, delivers the blood to a heat exchanger/pump assembly 40 that cools the blood and delivers the cooled blood, via the catheter, back to the patient. In one arrangement, the catheter of the blood-cooling device 26 includes physiological sensors and that provide physiological information to the physiological monitor of the life support console 105 and resuscitation console 104.

FIG. 13 illustrates an arrangement of a console 1 docked to a base station 2 where the console 1 includes a console thermal conductor 154 configured as a liquid gas evaporator 190 and the base station 2 includes a thermal regulation source 158 configured as a liquid gas source 204, such as a cryogen tank. In another arrangement, the console 1 and base station 2 are integrated into a single unit. As such, when the user transports the console 1 to a patient, the user transports both the liquid gas evaporator 190 and the liquid gas source 204 as a single unit to a patient location.

What is claimed is:

1. A thermal delivery system comprising:
a base station having a base station thermal conductor and a thermal regulation source in thermal communication with the base station thermal conductor; and
a console detachably coupled to the base station, the console having:
a reservoir configured to hold a fluid,
a console thermal conductor coupled to the reservoir and in thermal communication with the base station thermal conductor of the base station, the console thermal conductor configured to exchange thermal energy with the base station thermal conductor, and
a pump in fluid communication with the reservoir, the pump configured to deliver fluid from the reservoir to a body temperature regulation device when the console is detached from the base station.

2. The thermal delivery system of claim 1 wherein the base station thermal conductor and the thermal regulation source are configured to reduce a temperature of the console thermal conductor.

3. The thermal delivery system of claim 2 wherein the console comprises a sensor configured to detect a presence of ice relative to the console thermal conductor.

4. The thermal delivery system of claim 2 wherein the console comprises a heating element in thermal communication with the console thermal conductor.

5. The thermal delivery system of claim 2 wherein the body temperature regulation device further comprises a body-cooling device in fluid communication with the console.

6. The thermal delivery system of claim 5 wherein the body-cooling device comprises a head-cooling device.

7. The thermal delivery system of claim 5 wherein the body-cooling device comprises a blood-cooling device.

8. The thermal delivery system of claim 1 wherein the reservoir removably couples to the console.

9. The thermal delivery system of claim 1 wherein:
the base station comprises a power supply; and
the console comprises a battery in electrical communication with the pump and detachably coupled to the power supply of the base station.

10. The thermal delivery system of claim 1 further comprising a physiological sensor configured to detect a physiologic state of a subject.

11. The thermal delivery system of claim 10 wherein the physiological sensor is chosen from the group consisting of an electrocardiogram sensor, a temperature sensor, or a pulse oximetry sensor.

12. The thermal delivery system of claim 1 further comprising a treatment apparatus configured to provide a treatment to a subject.

13. The thermal delivery system of claim 12 wherein the treatment apparatus is chosen from the group consisting of a fluid infusion device, a defibrillator, or a ventilator.

14. A thermal delivery system comprising:
a base station having a thermal regulation source; and
a console detachably coupled to the base station, the console having:
a reservoir configured to hold a fluid,
a thermal conduction element coupled to the reservoir and in thermal communication with the thermal regulation source, and
a pump in fluid communication with the reservoir, the pump configured to deliver fluid from the reservoir to a body temperature regulation device when the console is detached from the base station.

15. The thermal delivery system of claim 14 wherein the thermal regulation source is configured to reduce a temperature of the thermal conduction element.

16. The thermal delivery system of claim 15 wherein the thermal regulation source comprises a liquid gas source and wherein the thermal conduction element comprises a gas evaporator.

17. The thermal delivery system of claim 16 wherein the pump comprises a turbine in fluid communication with the gas evaporator, the turbine configured to receive gas from the gas evaporator and cause operation of the pump.

18. The thermal delivery system of claim 15 further comprising a body-cooling device in fluid communication with the console.

19. The thermal delivery system of claim 14 wherein:
the base station comprises a power supply; and
the console comprises a battery in electrical communication with the pump and detachably coupled to the power supply of the base station.

20. A method for altering a body temperature of a subject comprising
coupling a console, holding a fluid, to a base station to allow the base station to alter the temperature of the fluid within the console;
detaching the console from the base station;
transporting the console to a subject location;
placing a body temperature regulation device, associated with the console, in thermal communication with at least a portion of the subject; and
activating the console to transmit the fluid within the console to the body temperature regulation device.

21. The method of claim 20 wherein the step of coupling comprises coupling the console to a first base station located at a first location and further comprising:
transporting the console to a second base station located at a second location, the second location distinct from the first location; and
coupling the console to the second base station to allow the second base station to alter the temperature of the fluid within the console.

22. The method of claim 20 further comprising defibrillating the patient.

23. A thermal delivery system comprising:
a base station having a base station thermal conductor and a thermal regulation source in thermal communication with the base station thermal conductor;
a console detachably coupled to the base station, the console having a pump motor and a console thermal conductor in thermal communication with the base station thermal conductor; and,
a fluid reservoir detachably coupled to the console and having a pump head detachably coupled to the pump motor, the fluid reservoir in thermal communication with the console thermal conductor.

24. The thermal delivery system of claim 23 further comprising a body temperature regulation device in fluid communication with the fluid reservoir.

25. The thermal delivery system of claim 23 wherein:
the base station comprises a power supply; and
the console comprises a battery in electrical communication with the pump motor and detachably coupled to the power supply.

* * * * *